US008437076B2

(12) United States Patent
Takanashi et al.

(10) Patent No.: US 8,437,076 B2
(45) Date of Patent: May 7, 2013

(54) FRONT-LENS ATTACHMENT FOR AN OPTICAL OBSERVATION DEVICE

(75) Inventors: Fumio Takanashi, Oberkochen (DE);
Markus Seesselberg, Aalen (DE);
Andrè Mueller, Koenigsbronn-Zang (DE); Peter Reimer, Ellwangen (DE)

(73) Assignee: Carl Zeiss Meditec AG, Jena (DE)

( * ) Notice: Subject to any disclaimer, the term of this patent is extended or adjusted under 35 U.S.C. 154(b) by 704 days.

(21) Appl. No.: 12/380,607

(22) Filed: Mar. 1, 2009

(65) Prior Publication Data
US 2009/0219483 A1 Sep. 3, 2009

(30) Foreign Application Priority Data
Feb. 28, 2008 (DE) .......................... 10 2008 011 608

(51) Int. Cl.
*A61B 3/10* (2006.01)
*G02B 21/00* (2006.01)

(52) U.S. Cl.
USPC .......................................... 359/381; 351/216

(58) Field of Classification Search .................. 359/368, 359/381, 384, 656–661; 351/216–218, 233–236
See application file for complete search history.

(56) References Cited

U.S. PATENT DOCUMENTS

| 5,311,365 | A |   | 5/1994 | Klearman et al. |
| 5,793,524 | A | * | 8/1998 | Luloh ........................... 359/381 |
| 5,886,812 | A |   | 3/1999 | Volk |
| 6,421,173 | B1 | * | 7/2002 | Corbisiero et al. ........... 359/372 |
| 6,943,942 | B2 |   | 9/2005 | Horiguchi et al. |
| 7,092,152 | B2 | * | 8/2006 | Kirchhuebel ................. 359/381 |
| 7,379,239 | B2 | * | 5/2008 | Strobel et al. ................. 359/384 |
| 2002/0118448 | A1 | * | 8/2002 | Kirchhuebel et al. ........ 359/368 |

FOREIGN PATENT DOCUMENTS

| DE | 82 27 304 U1 | 12/1982 |
| DE | 92 17 517 U1 | 2/1993 |
| DE | 94 15 219 U1 | 11/1994 |
| DE | 297 12 376 U1 | 11/1998 |
| DE | 200 17 891 U1 | 2/2001 |
| DE | 202 15 635 U1 | 12/2002 |
| EP | 1 447 698 A2 | 8/2004 |
| EP | 1 450 194 A2 | 8/2004 |
| WO | WO 2004/019107 A1 | 3/2004 |
| WO | WO 2006/002961 A1 | 1/2006 |

* cited by examiner

*Primary Examiner* — Darryl J Collins
(74) *Attorney, Agent, or Firm* — Kriegsman & Kriegsman

(57) ABSTRACT

The present invention, among other things, relates to a front-lens attachment (20) for an optical observation device (10), in particular for a microscope. The front-lens attachment (20) has a retaining element (38) that has a retaining element (32), on which at least one lens element (33, 34) is disposed. Further, it provides a positioning device (21) for positioning the retaining element (32) and the at least one lens element (33, 34) disposed thereon, relative to the optical observation device (10), whereby retaining device (32) is disposed on positioning device (21). Finally, a fastening means (35) for fastening the retaining device (38) to the front-lens attachment (20) is provided. In order to be able to provide such a front-lens attachment (20) in a structurally simple and cost-effective manner, it is provided, for example, that positioning device (21) has at least two positioning components (22, 28), which are joined together via a joint (31).

31 Claims, 21 Drawing Sheets

FRONT-LENS ATTACHMENT FOR AN OPTICAL OBSERVATION DEVICE

BACKGROUND OF THE INVENTION

The present invention first relates to a front-lens attachment for an optical observation device according to the preamble of patent claim 1 as well as to the preamble of patent claim 7. In addition, the invention also relates to a turret attachment for the rotatable arrangement of at least two lens elements on a front-lens attachment for an optical observation device, an optical observation device as well as the special use of such a front-lens attachment or optical observation device.

Optical observation devices may involve, for example, microscopes, e.g., operating microscopes, in particular operating microscopes for ophthalmology, or the like. Such microscopes, among other things, usually have a microscope body with different optical elements and a tube piece. In addition, microscopes usually have at least one objective element. Not rarely, front-lens attachments are fastened in the region surrounding the objective element of the microscope.

Front-lens attachments for microscopes are already known in different embodiments. They usually serve for the purpose of introducing additional lens elements into a beam path of the microscope. A field of application for such front-lens attachments is the field of indirect ophthalmoscopy.

The retina or regions of the vitreous body of an eye can be imaged by means of an additional optical component in the form of at least one lens element, for example, a highly refractive single lens or group of lenses, which is positioned as defined, in front of the eye. The image of the back segment of the eye that is obtained in this way can be observed, if necessary, with appropriate observation devices, in particular with a stereoscopic operating microscope. Thus, the position of the image is dependent on the ophthalmoscopic magnifying lens used, particularly with respect to its refractive power, on the refractive error of the eye to be observed, e.g., near-sightedness or farsightedness, on the region/segment of the eye that is under observation, for example, the retina, regions of the vitreous body at a distance x over the retina or the like, on anomalies of the eye, for example, "liquid/oil-filled", "gas-filled" natural vitreous body; phakic, "aphakic", "pseudophakic" [intraocular lenses] and the like, on the distance between the ophthalmoscopic magnifying lens and the patient's eye, and similar dependencies.

By means of the front-lens attachment, the optical component is placed either directly onto the eye to be observed, for example, in the form of an indirect contact lens, or is held suspended at a certain distance in front of the eye to be observed, for example, by means of an indirect ophthalmoscopic magnifying lens in the "non-contact" region.

Depending on the optical properties of the ophthalmoscopic magnifying lens or of the contact lens, large, wide-angle regions of the fundus of the eye can be observed in this way, e.g., by magnifying lens or magnifying glasses with high refractive power, or, on the other hand, smaller regions of the fundus of the eye that are highly resolved can be observed by magnifying lens or magnifying glasses with lower refractive power. For an optimal or frame-filling image, each ophthalmoscopic magnifying lens or each contact lens shall be positioned at a specific distance from the eye, a distance that depends on the refractive power of the lens, since if it is not, vignetting due to the iris or similar effects may occur.

Different limiting conditions during a surgical operation, such as, for example, the fittings of the ophthalmoscopic magnifying lens, the accessibility and the working space in the vicinity of the eye of the patient, and similar conditions make it necessary, under certain circumstances, to move the ophthalmoscopic magnifying lens away from the eye, in particular, in the case of ophthalmoscopic magnifying lenses with very short focal lengths which usually must be positioned very closely to the eye. Because of this, the position of the (intermediate) image is shifted and this also leads to vignetting.

For example, such a front-lens attachment for a microscope is described in German Utility Model G 94 15 219 U1. The microscope involves an operating microscope for ophthalmology for observation of an eye. Among other things, the microscope has a principal objective, in the vicinity of which is attached the front-lens attachment. The known front-lens attachment has a holding or retaining device in the form of a retaining arm on which a lens element is disposed, which can be swung as desired into the beam path passing through the objective. For this purpose, the retaining arm is attached to a positioning device, which involves a rod assembly. First of all, the retaining arm, and with it the lens element, can be swung around the rod assembly. In addition, another linear drive is provided. The rod assembly can be moved via this linear drive in the lengthwise direction parallel to the optical axis. The retaining arm, and with it the lens element, can thus also be moved via the rod assembly in the lengthwise direction parallel to the optical axis, so that the position of the lens element can be moved on the optical axis between the objective and the eye to be observed. The positioning device is attached to the microscope via a fastening device, which is formed as an adapter in the known solution. The fastening device is designed in such a way that the entire front-lens attachment can be swung out of the beam path.

Whereas a front-lens attachment is described in G 94 15 219 U1 by which it is possible to introduce a single lens element as desired into the beam path, a front-lens attachment with a similar construction is described in U.S. Pat. No. 6,943,942 B, by which means it is also possible to introduce two lens elements selectively into the beam path. This known solution provides for the presence of two lens elements, each of which is attached via its own retaining device in the form of a retaining arm to a positioning device in the above-depicted manner. This known solution aims at being able to temporarily swing a second lens also into the beam path of the microscope, in order to manipulate the refractive power of the lens element in such a way that the front segment of the eye can be observed.

The previously known solutions, of course, have a number of disadvantages. Thus, for a known front-lens attachment, as is described, for example, in U.S. Pat. No. 5,793,524 B, a relatively large structural space is required, since a linear movement of the lens element must be conducted in the lengthwise direction and thus parallel to the optical axis. Focussing via a linear movement of the lens element relative to the observation device and thus to the eye of the patient represents great disadvantage. During focussing, the position of the pupil also changes simultaneously. If, for example, the position of the pupil of the observation device lies too far removed from the entrance pupil of the eye of the patient, there is an undesired vignetting, since the visible region of the fundus of the eye will become smaller. The alignment and focussing is thus an iterative process. Even if the lens element is swung out of the beam path, or is found in a position in the vicinity of the objective, the structural space cannot be reduced, since the positioning rod assembly and the linear drive remain unchanged in their lengthwise extension and positioning. The front-lens attachment in and of itself is also formed with a relatively large volume due to the linear drive. This also has various disadvantages. If, for example, the front-lens attachment is completely swung out horizontally, as this is described as being possible in G 94 15 219 U1, a considerable empty space is necessary, into which the front-lens attachment can be swung in. In addition, it is also difficult to clean the front-lens attachment and, if needed, to sterilize it. If microscopes are employed as operating microscopes, then front-lens attachments must be sterilized after use, which is usually carried out in an autoclave. Large, complex and bulky components can be sterilized only with great difficulty in an autoclave.

In addition, the known solutions are complex in their construction and are thus expensive, particularly since a separate drive must be maintained. Such drives, which for the most part function electrically can also be sensitive to interference.

SUMMARY OF THE INVENTION

Starting from the named prior art, the object of the present invention is to enhance a front-lens attachment of the initially named type in such a way that it can be realized in a structurally simple and cost-effective manner. In this way, by means of the front-lens attachment according to the invention, an improved handling and operability will also be achieved. In addition, a correspondingly improved observation device shall be provided.

This object is achieved according to the invention by the front-lens attachment with the features according to the independent patent claim 1 as well as the independent patent claim 7, the turret attachment with the features according to the independent patent claim 19, the optical observation device with the features according to the independent patent claim 23 and the independent patent claim 24, as well as the special use according to the independent patent claim 29. Further features and details of the invention result from the subclaims, the description and the drawings. Here, features and details which are described in connection with the front-lens attachment according to the invention, of course, also apply in connection with the optical observation device according to the invention, and vice versa, so that reference is made each time interchangeably to the full content of the corresponding statements. The same applies in a corresponding manner relative to the turret attachment according to the invention as well as the use according to the invention.

According to the present invention, first of all, an improved front-lens attachment for an optical observation device, in particular for a microscope, is provided.

The front-lens attachment according to the invention is structurally simple to produce and is designed in a space-saving manner, particularly if a lens element is not required. This feature is of particular advantage when the front-lens attachment needs to be cleaned, for example, in an autoclave. This design makes the front-lens attachment easy to handle and to operate.

The present invention provides a front-lens attachment which is suitable for an optical observation device. The invention is not limited, however, to specific types of optical observation devices. For example, the front-lens attachment can be used for a microscope, e.g., an operating microscope, particularly an operating microscope for ophthalmology.

A front-lens attachment shall be understood as an attachment that is disposed in front of at least one specific component of the optical observation device. If, for example, the optical observation device involves a microscope, this specific component is usually an objective element. Advantageously, a front-lens attachment can be designed in such a case for the purpose of being introduced in front of the objective or in the region surrounding the objective, in order to particularly influence a beam path that passes through the objective. For example, the front-lens attachment may involve a separate device that is produced independently from the optical observation device and that can be fitted to the optical observation device as needed. Of course, the front-lens attachment can also be designed as a fixed component of the optical observation device. Meanwhile, if the front-lens attachment needs to be cleaned, it is advantageous if it is disposed in a detachable manner to the optical observation device.

The front-lens attachment according to the invention first has a holding or retaining device. The retaining device has a retaining element on which is disposed at least one lens element. Here, the invention is generally not limited to specific embodiments for the retaining device and the retaining element. Likewise, the invention is generally not limited to a specific number of lens elements, specific types of lens elements or specific positions and arrangements of the lens elements on the retaining element. Different advantageous, but non-exclusive examples of this will be explained in detail in the further course of the description.

The retaining element can be designed advantageously as a type of turret attachment or a component of such a turret attachment. This type of turret attachment will be explained in more detail in the further course of the description. The turret attachment generally serves for the purpose of being able to swing the lens element into a beam path. According to the present invention, it is particularly advantageously provided that only one lens element from a selection of lens elements is always swung into the beam path, and this is performed by an appropriate rotation of the turret attachment.

Another basic feature of the front-lens attachment according to the invention is a positioning device. First of all, the positioning device is characterized in that the retaining element for the at least one lens element is disposed on the positioning device. Here, the invention is not limited to specific embodiments of where and how to attach the retaining element to the positioning device. Several advantageous, but non-exclusive examples of this will be explained in more detail in the further course of the description.

The positioning device serves for positioning the retaining element and the at least one lens element that is disposed on it, referred to an optical observation device and/or a focussing device, which will be described in more detail below. This means that the retaining element and the at least one lens element disposed thereon can be brought into a desired position via the positioning device, in which the lens element particularly can fulfill its provided function. Depending on the application objective and the field of application of the front-lens attachment each time, different requirements can be placed on the positioning device and its configurations.

It is advantageously provided that the positioning device is designed in a way that it can adjust discrete positioning states. It is preferably provided that only two positioning states can be adjusted by means of the positioning device, i.e., a park position (for example, when the device is folded up) and a working position (in a state where the device is spread apart).

How the positioning can be carried out relative to the optical observation device and/or the focussing device will be illustrated on the basis of an example, but the invention is not limited to this concrete example. For example, it can be provided that the optical observation device involves a microscope with an objective, as has already been mentioned. Now, if the front-lens attachment will be used for the purpose of introducing an additional lens element selectively into the beam path which passes through the objective, it is the function of the positioning device, the retaining element and the at least one lens element disposed thereon to be placed in front of the objective and thus related to the latter, so that the lens element can be introduced into the beam path.

The field of application of the front-lens attachment preferably lies in indirect, contact-free ophthalmology, but also, as needed, to support indirect ophthalmology with contact, in particular with the use of a focussing device. The front-lens attachment advantageously serves for observing an intermediate image by means of an optical observation device, preferably by means of a stereoscopic operating microscope for ophthalmology, during a surgical intervention on the eye, in particular in the field of fundus surgery.

According to the first aspect of the invention, a front-lens attachment is provided for an optical observation device, in particular for a microscope, with a focussing device and with a retaining device, having a retaining element on which is disposed at least one lens element, as well as further having a positioning device for positioning the retaining element and the at least one lens element disposed thereon relative to an optical observation device and/or the focussing device, wherein the retaining element is disposed on the positioning device. The front-lens attachment is characterized according to the invention in that at least one covering cap is provided for the focussing device, on which the retaining device is attached via a fastening means and that the at least one covering cap is joined to the focussing device.

In addition to the previously described basic features of the front-lens attachment, the front-lens attachment according to the first aspect also has a focussing device. The focussing device generally involves a focussing optics, which is designed, for example, as a reducing optics.

It is advantageously provided that the focussing device is designed as a component of the front-lens attachment. Preferably, it involves a separate component, which represents a component of the front-lens attachment. Of course, the focussing device or its functions can also be integrated into the optical observation device, e.g., into a microscope. Such an example is explained in more detail below in connection with the optical observation device.

Advantageously, the front-lens attachment can be or will be attached to the optical observation device via the focussing device. Here, a detachable connection is particularly preferred. How this can be realized in its individual steps will be described in greater detail below on the basis of several advantageous, but non-exclusive examples.

Usually, the focussing device is not sterile or cannot be sterilized, since a sterilizing capacity is often not required or desired. If the optical observation device involves an operating microscope, however, a sterilization after use is necessary. For this purpose, the front-lens attachment according to the invention has at least one covering cap for the focussing device. The covering cap is joined to the focussing device, so that operating controls and regions of the focussing device at risk of contact in particular are protected by a covering cap, particularly one that can be sterilized. This has the advantage that complex, expensive, sensitive components are not subjected to the high stress of cleaning, disinfection, sterilization. Appropriately complex or even sensitive mechanical and optical components or assemblies as well as electronics can be integrated without problem into the structure of the focussing device and motor drives will be used, for example, for motor-driven functions such as focussing, control or monitoring functions, and the like.

Since the focussing device is covered by the covering cap, the focussing device does not need to be sterilized. Rather, it suffices if the covering cap is sterilized. The covering cap particularly has the advantage that it can be sterilized. The ability to be sterilized is absolutely necessary when used for surgical purposes. The sterile cap offers protection or covering of the regions of the focussing device at risk of contact, which have a non-sterile region, and thus makes possible the sterile use of the front-lens attachment during surgery. In order to assure the sterile operation of the front-lens attachment, a relatively simple and cost-effective assembly of components is used, wherein the cleaning, disinfection and sterilization of this assembly is essentially simpler than the cleaning, disinfection and sterilization of the entire front-lens attachment. When conducting several surgical interventions successively, several sterile systems are required. For this purpose, several sets of sterile covering caps and lens elements, for example, ophthalmoscopic magnifying lenses must be ready or must be available as well as incomplete systems with sterilized focussing or reducing optics and drive unit. The sterile covering cap can be temporarily placed on the region of the focussing device, which is advantageously moveable, under sterile conditions during surgery, and even several times as needed. By placing the covering cap on the focussing device, the covering cap can be locked, for example, so that it is aligned with the focussing device and is secured against undesired loosening of the focussing device during surgery. The covering cap can be loosened, for example, unlocked, by means of two operating controls or press points on the cap, for example, and thus it is possible to remove the covering cap from the focussing device under sterile conditions during surgery. The covering cap, particularly the sterile cap, can be placed on the region of the focussing device, for example, the moveable region, advantageously by means of a form-fitting connection. The covering cap can be fixed or locked relative to the focussing device, for example, by means of two spring-loaded catch elements on the focussing device, each of which engages in an undercut or slot in the sterile part of the covering cap. In order to unlock and remove the covering cap from the focussing device, advantageously, two deformable elastic regions on the sterile covering cap are deformed in such a way that the locking elements of the focussing device are moved and thus the cap is unlocked and can be removed from the focussing device.

In addition to covering the focussing device, the covering cap also serves for the purpose of fastening the retaining device to it by means of a fastening means. In addition, the front-lens attachment consequently provides a fastening means, by means of which the retaining device can be fastened to the covering cap. The specific details of how this can be performed will be explained more closely in the further course of the description, particularly also in connection with the optical observation device according to the invention which is also described further below. For example, the fastening means can be designed in such a way that a connection is brought about that can be loosened and/or pivoted and/or rotated and/or moved linearly.

A front-lens attachment according to the present invention may be comprised of three basic components, for example: a focussing device, a sterile covering cap and a retaining device for optical elements for imaging the fundus of the eye, e.g., for generating an intermediate image, and at least one lens element, e.g., an ophthalmoscopic magnifying lens. When a lens changer is used, this involves the retaining element of the retaining device, on the covering cap, and several lens elements, for example, ophthalmoscopic magnifying lenses, may also be used.

The covering cap can be advantageously joined to the focussing device in a detachable manner. The covering cap may be introduced temporarily and then taken off again, i.e., several times as needed during a surgical intervention and under sterile conditions, by means of such a joining, e.g., a suitable coupling site on the focussing device. A fixing mechanism, for example, a locking mechanism for the covering cap, is advantageously also integrated into the focussing device.

Advantageously, the focussing device may have at least one optical component for focussing an observation device on the intermediate image of at least one lens element.

The focussing device contains additional optical components for focussing the observation device, also called focussing optics in the following, on the intermediate image of the lens element, for example, an indirect ophthalmoscopic magnifying lens which is operated in "non-contact" or "contact" mode. The focussing optics advantageously consists of at least one, preferably fixed, negative component and at least one positive component that is preferably movable. Focussing can be conducted either manually or can be motor-driven. The focussing optics is advantageously designed so that the observation device that is used, for example, the microscope, can be focussed with the focal length f in a range of f1 ... f2.

Typically $f1 \approx f{-}7$ mm & $f2 \approx f{-}50$ mm; ideally $f1{=}0$ & $f2{=}f{-}60$ mm; the range f1 ... f2 thus covers the intermediate image planes for typical ophthalmoscopic magnifying lenses and contact lenses, e.g., 40 D ... 130 D below the usual conditions of use, such as typical distances between the ophthalmoscopic magnifying lens and the eye of the patient; phakic/pseudophakic/aphakic [IOL]; eyeball with natural vitreous body/oil-filled/gas-filled; near-sighted or far-sighted patient eye; observation of the retina or regions in the vitreous body at a distance x over the retina; and the like.

Therefore, the focussing movement is decoupled from the movement of the lens element, for example, of the ophthalmoscopic magnifying lens, relative to the eye of the patient. The distance between the ophthalmoscopic magnifying lens and the patient's eye usually affects the visible region of the fundus of the eye from the intermediate image. An optimal sterile covering cap and retaining device will now be provided. The system can thus be aligned and focussed in an essentially simpler manner, e.g., with respect to a positioning of the ophthalmoscopic magnifying lens relative to the patient's eye. With an appropriate positioning of the lens element, for example, of an ophthalmoscopic magnifying lens or a contact lens, the fundus of the eye can be observed under the most varied conditions and with different lens elements without changing the position of the observation device, so that the distance from the patient's eye to the microscope remains unchanged. A rapid and uncomplicated change between observing the front of the eye and the fundus results from this, as well as a reduction in the risk of a collision between the device and the patient or patient's eye.

In addition, however, a surgeon also can deliberately manipulate the distance from the ophthalmoscopic magnifying lens to the patient's eye by moving the entire system. This is of interest, for example, if the lens element is too close to the eye of the patient and thus interferes with or obscures the view when working with surgical instruments in the eye; this is particularly a problem with ophthalmoscopic magnifying lens of short focal length that are thus highly refractive.

The retaining device will now be explained in greater detail below.

It can be advantageously provided that the retaining device is disposed in a detachable manner on the covering cap. In another configuration, it can be provided that the retaining device is disposed in a rotatable and/or pivotable and or linearly movable manner on the covering cap.

It is preferably provided that the positioning device of the front-lens attachment is designed in a special manner. It is advantageously provided for this purpose that the positioning device has at least two positioning components, which are joined together via a joint or articulation. In the simplest case, it is sufficient if two positioning components are provided, which are joined together via a joint. Of course, cases of application are also conceivable, in which the positioning device has more than two positioning components, whereby a joint element is provided between every two adjacent positioning components.

The invention is generally not limited to specific embodiments for the positioning components. Several advantageous, but non-exclusive examples of these will be explained in more detail in the further course of the description. Likewise, the invention is not limited to the use of specific types of joints. In the present case, a joint or articulation generally is understood as a movable connection between two units, whereby the units involve the positioning components. Several advantageous, but non-exclusive examples of suitable types of joints will be explained in more detail in the further course of the description.

According to a second aspect of the invention, a front-lens attachment is provided for an optical observation device, particularly for a microscope, with a retaining device having a retaining element on which is disposed at least one lens element, a positioning device for positioning the retaining element and the at least one lens element disposed thereon relative to an optical observation device, wherein the retaining element is disposed on the positioning device, and with a fastening means for attaching the retaining device to the front-lens attachment. This front-lens attachment is characterized according to the invention in that the positioning device has at least two positioning components, which are joined together via a joint or articulation. For the basic construction of the front-lens attachment as well as for its basic mode of operation, reference is also made to the full extent to the statements above relative to the first aspect of the invention.

The front-lens attachment of the invention according to the two aspects has a number of advantages in comparison to the solutions known from the prior art. Thus, first of all, the front-lens attachment is constructively simple to manufacture, especially since complex structures such as linear drives or the like can be dispensed with. Likewise, the structural space necessary for the front-lens attachment can be reduced, so that the front-lens attachment can be introduced in a space-saving manner, on the one hand, on an optical observation device. This particularly applies when the at least one lens element disposed on the front-lens attachment is occasionally not necessary In addition, the space-saving configuration also has the advantage that the front-lens attachment can be cleaned in a simple way, as necessary. Cleaning can be conducted by first employing a mechanical cleaning, for example, in at least one washing device, followed by disinfection in a solution bath as well as sterilization in an autoclave.

Advantageously, with such an embodiment, the retaining device can be disposed on the front-lens attachment in a detachable manner. In another configuration, the retaining device can be disposed in a rotatable and/or pivotable and or linearly movable manner on the front-lens attachment.

As was also stated above, the invention is not limited to specific types of joints for joining the positioning components. Several advantageous configurations will be named below for this purpose. The positioning components can be joined together preferably by means of a rotating joint. A rotating joint is generally characterized in that the two positioning components can be rotated relative to one another via this rotating joint. It is thus advantageously provided that the rotating joint is comprised of two joint elements, each of which is provided at one end of the positioning components. For example, such a rotating joint could be realized by providing bores or openings generally in the ends of the positioning components that are to be joined, through which a bolt-type element can be passed. The positioning components in this configuration rotate around a common axis of rotation. A joint could be configured in a similar way, for example, also as a screw joint, as a hinge joint or the like. Of course, it is also conceivable that the joint is formed as a ball joint. If the positioning device provides several positioning components and thus also several joints, each joint may be of the same type, but also joints of different types may be employed.

It is advantageously provided that the joints are designed in such a way that they permit the rotation of one positioning component relative to the other positioning component by a specific angle of rotation. The angle of rotation then involves the aperture angle of the two positioning components. It can be advantageously provided that the joint element is configured in such a way that it is possible to form an angle of rotation or an aperture angle of the positioning components of less than 90 degrees, preferably in a range between 40 and 80 degrees. The reason for this is a safety function, for example, in order to avoid an undesired contact with the patient or the patient's eye. The angle of rotation basically influences the position of the lens elements. Therefore, it is preferred that a rotation is allowed by means of the joint such that a defined, reproducible end position and rest position (for example, in a folded-up state) can be realized.

In a preferred configuration, it can be provided that the front-lens attachment has a positioning device with two positioning components, that a first positioning component is disposed so that it can be pivoted via a fastening means in at least a first pivoting direction on the optical observation device or on the front-lens attachment or on the covering cap, and that a second positioning component is disposed on the first positioning component so that it can be pivoted via a joint in at least a second pivoting direction differing from the at least one first pivoting direction.

The positioning device can rotate around the optical axis by means of a rotating joint. A lens element that has been swung in thus also remains coaxial to the optical axis. The position of the positioning components, which represents a kind of scissor-like arrangement, as well as the position of the retaining element therefore can be adapted to the working space conditions and the preferences of the surgeon during the surgical intervention, in particular when working on the fundus.

By means of the positioning components, which form a type of scissors mechanism in such an arrangement and which then preferably have two defined end positions, i.e., a "folded-up locked position" and a "spread-apart end-stop gravitation", the retaining element and with it each of the lens elements found thereon can be positioned in a defined manner. With spread-apart positioning components, which are advantageously held in this position at end stops due to gravitation, and a swung-in retaining element, the lens element is positioned in a defined, fixed distance to the observation device and coaxial to the optical axis, advantageously by means of a specific type of mount. In this way, the lens element mount and the lens element holder are advantageously adapted to the observation device that is employed so that the respective lens element, when it is spread apart, assumes an optimal distance to the patient's eye, for example, for a frame-filling imaging of the fundus of the eye without vignetting, if the observation device has been focussed onto the plane of the "iris of the patient's eye" prior to swinging in the lens element and the focussing device. In this manner, it is assured that the position of the entrance pupil of the observation device and the pupil of the patient's eye lie next to one another.

Folding or bending the lens element holder increases the safety range, i.e., the free run, in the case of a collision between the ophthalmoscopic magnifying lens and the patient or the patient's eye due to an unintentional or erroneous movement of the entire system.

The lens element holder arrangement can be made compact, folded up, particularly minimized in structural space, whereupon few disruptive contours are formed. In addition, the focussing optics, retaining element and lens element mount are mutually adapted to one another and this leads to the above-named advantages in application, such as, for example, decoupling the movements for pupil position—visible range—and focus. Additionally, the risk of collision with the patient is reduced, since the entire system no longer must be moved. Also, a rapid changing between front and back segments is possible.

By means of an additional rotating joint and a special uptake for the lens elements, for example, an uptake for several different ophthalmoscopic magnifying lenses, different ophthalmoscopic magnifying lenses can be swung into the beam path of the optics, alternatively for short times, even during surgery, and also several times, even under sterile conditions, or all ophthalmoscopic magnifying lenses can be swung out away from the beam path by means of an appropriate intermediate positioning. The lens element changer, the retaining element, is advantageously configured so that the respective ophthalmoscopic magnifying lens(es), which is/are not required, obstruct the structural space below the observation device as little as possible. This is advantageously achieved by an appropriate angular arrangement of the rotating joints and bending of the lens element mounts.

The use of an ophthalmoscopic magnifying lens changer, a retaining element, makes possible the alternate, non-simultaneous swinging in of different ophthalmoscopic magnifying lenses as well as the swinging out of (all) ophthalmoscopic magnifying lenses from the beam path of the observation device with swung-in focussing optics, preferably with the use of contact lenses.

The retaining element and the lens elements, in particular their mount, are thus advantageously configured so that the lens elements, depending on their refractive power, can be positioned at different, defined distances to the observation device or to the patient's eye.

As was mentioned also above, the positioning device, and in particular its positioning components, can be designed in different ways. For this purpose, several advantageous, but non-exclusive embodiments will be described below. It can be advantageously provided that the positioning device has a first positioning component, which has on its one end a joint element for connecting the joint with a second positioning component, and that the fastening means is provided on the other end of the first positioning component. It can be provided advantageously in another configuration, alternatively or additionally, that the positioning device has a second positioning component, which has on its one end a joint element for connecting the joint with a first positioning component, and that the retaining device is disposed on the other end of the second positioning component. For example, in such a case, the positioning components can be designed in the form of a longitudinally extended unit and, in particular, [may have] a rod-shaped contour.

The positioning components can be joined together preferably by a joint, in such a way that they can be folded up into one another or spread apart. In this way, it is possible that when the positioning components are in the folded-up state, the front-lens attachment has only a small space requirement. Such a folded-up state is then particularly selected if the at least one lens element is not required and thus is found in a type of park position. In this case, the front-lens attachment does not hinder the operator of an optical observation device to which the front-lens attachment is fastened.

Advantageously, it can be provided that the positioning device has two positioning components, that a first positioning component has two legs that are distanced from one another and bound an uptake space, and that the other, second positioning component is joined with the first positioning component via the joint in such a way that it can be folded into this uptake space. In such a case, the joint can preferably be formed as a rotating joint, as has been described above.

As has also been described above, the invention is not limited to a specific number of lens elements or to specific types of lens elements. In this respect, several advantageous, but non-exclusive examples will be explained below.

If the front-lens attachment is used, for example, on an operating microscope for ophthalmology, for observing an eye to be operated on, for operations on the retina or on the vitreous body, the surgeon requires views in which he can well view the center of the retina up to its peripheral regions. in such a case, different types of lens elements are necessary. For example, a lens element with a small diopter number from 30 D to 60 D is ideal for a large magnification and a high resolution. A lens element with high diopters between 90 D and 120 D is ideal, for example, for a good wide-angle observation.

Basically, it is sufficient for the present invention if only a single lens element is provided on the retaining element. As has been described above, however, there are also cases of application, in which two or more lens elements are advantageous.

It can thus be advantageously provided that two or more lens elements, which are preferably detachable, are disposed on the retaining element. In this way, it can be provided, for example, that a lens element with a small diopter number and a lens element with a high diopter number, as described above, are used. Therefore, two lens elements of different types can be provided by means of the front-lens attachment, for example, a lens element for a high resolution and a lens element for a good wide-angle observation. During an operation, the surgeon can select the lens element desired each time, for example, by rotating the retaining element. This is of advantage, particularly in those operations during which a switching between different lens elements must be made frequently.

It can be advantageously provided that at least one lens element is designed as an ophthalmoscopic magnifying lens.

Ophthalmoscopic magnifying lenses are usually comprised of a simple, often aspherical lens. They usually have no contact with the patient's eye—the distance to the patient's eye is dependent on the properties of the magnifying lens and preferably lies at approximately 3 to 25 mm, and they can be cleaned/sterilized in a simple manner. They are preferably used for surgical interventions, in fact, due to their "non-contact" property and the fact that they can be sterilized.

Ophthalmoscopic magnifying lenses advantageously consist of the lens and a lens mount with a coupling place/uptake for the lens holder—for fastening to a retaining element. The properties of the lens are advantageously adapted to the requirements in fundus surgery and are essentially different in their refractive power. Depending on the refractive power of the lens, each ophthalmoscopic magnifying lens must be positioned in a defined position relative to the patient's eye, in order to optimally image the back segment or fundus of the patient's eye, i.e., in a frame-filling manner. The retaining element is found in the swung-in state at a defined distance to the observation device or to the patient's eye. The differences in distances between the different ophthalmoscopic magnifying lenses are taken care of, for example, by means of various bendings of the lens mount.

If the lens elements swing out of the beam path of the operating microscope, so-called contact lenses may also be employed in a particularly simple way. Contact lenses for the most part consist of several lenses/groups of lenses. They have direct contact with the patient's eye, they can be optimized and employed in a targeted manner relative to their optical imaging properties, but for the most part they cannot be sterilized or can only be sterilized in a very complicated manner. Contact lenses are preferably employed in diagnostics or for monitoring.

It can be advantageously provided that the at least one lens element is disposed in a fixed manner on the retaining element. In another configuration, it is also conceivable that at least one lens element is disposed on the retaining element in a variable position, for example, it can be moved. It is also possible that the retaining element forms a type of uptake for the lens, on which the at least one lens element can be fastened in detachable manner by means of a lens holder. This can be provided, for example, by being able to plug the lens holder into the retaining element.

The invention is not limited to specific embodiments for the retaining element. Several preferred embodiment examples for retaining elements will be described below.

For example, the retaining element can be formed as a retaining arm. In this case, the at least one lens element is advantageously disposed at the end of the retaining arm. If two or more lens elements are employed, the retaining arm may have two or more arm regions projecting away from the attachment point relative to the attachment point of the retaining arm on the positioning device, whereby a lens element is disposed each time at the end of such an arm region.

In another configuration, it can be provided that the retaining element is designed in the form of a lens uptake. The lens elements are fastened to this lens uptake. Appropriate lens holders are provided for this purpose, to which are fastened or on which are held the lens elements, advantageously by means of a lens mount. The lens elements are then fastened to the lens uptake by means of the lens holders, preferably in a detachable manner, e.g., by means of a plug connection.

In the simplest case, the retaining arm or the at least one lens holder may have a straight contour. However, retaining arm contours or lens holder contours are also advantageous, in which the retaining arm or the arm regions of the retaining arm or of the lens holder have an angular and/or curved, and/or bent course, at least in regions. A bent course in this case shall be particularly also understood to mean a two-angle, bent-out course. In the last-named cases, in particular, it can be achieved by such a non-linear course that such lens elements, which are not necessarily straight, can be closely fitted to the optical observation device, so that they do not project out of the working field of the optical observation device and also do not act in a disruptive manner in the working field, so that the operator is not disturbed. If the retaining arm does not have a straight course, as described above, then this course is advantageously adapted to the contour and geometry of the optical observation device, for which the front-lens attachment will be employed. The arm regions may, of course, also be designed as the lens holder described further above, which then can be combined with a retaining element designed as an uptake.

The retaining element, for example, in the form of a retaining arm or a lens uptake, represents the uptake for the lens elements and serves for the mounting/uptake of the lens elements, for example, of the ophthalmoscopic magnifying lenses, during use. When a retaining element which represents a type of lens-element changer is used, it contains at least two uptake positions. The lens elements can then be inserted into or removed from the retaining element, for example, if they have an appropriate mount. It is assured that they are simple to clean and sterilize due to the configuration of the retaining element. By means of an additional coupling site, the lens elements can be removed from the retaining element for sterilization and the like, for example, they can be removed from their holder, e.g., if the lens elements are to be treated again by other cleaning/sterilization methods. In this way, the retaining element, for example, a changer with different pairings of lens elements, can be configured, e.g., for rapid and uncomplicated use during a surgical intervention.

It is thus preferably provided that the at least one lens element is disposed on the retaining element in a detachable manner.

The different distances specified for the lens elements relative to the observation device or to the patient's eye are advantageously provided by mounts that are specific for the lens elements, advantageously with different bends.

It can be advantageously provided that the retaining element is disposed in a rotatable manner on the positioning device. In this way, the lens element can be comfortably rotated into the desired working position. If the retaining element has two or more lens elements, the one that is specifically necessary can be comfortably rotated into the working position in this way. The retaining element may also be advantageously rotated or be able to be rotated into a position in which no lens element is found in the working position, for example, in a specific beam path. Such a position can be designated as a neutral position or park position. In such a position, it is then simply and comfortably possible to work with the contact lenses that are described further above.

If the retaining element is disposed in a rotatable manner on the positioning device in such a way, this retaining element can be designated as a type of turret attachment or a component of such a turret attachment. This type of turret attachment will be described further below in greater detail, so that in this respect, relative to such an advantageous configuration of the front-lens attachment, reference is made in the full extent to the corresponding statements for the turret attachment.

If the front-lens attachment is utilized for an operating microscope for ophthalmology, for example, and is used as a fundus imaging system, for example, a park position can be adjusted in which the front-lens attachment is folded against the microscope and wherein the—preferably angular—retaining element for the lens elements, which may involve, for example, ophthalmoscopic magnifying lenses, will be suitably rotated so that none of the lens elements is found in the beam path. This also makes it possible for a surgeon to use so-called contact lenses for surgery on a patient's eye. These involve lens elements that are directly applied to the patient's eye and which are not taken up in a mount that is attached to the operating microscope.

When the front-lens attachment is used in conjunction with an operating microscope, for example, an operating microscope for ophthalmology, the surgical time necessary can be shortened by the use of the front-lens attachment. The surgeon can find the necessary lens element simply and rapidly, and insert it preferably by rotation of the retaining element. A single system can now cover all different types of surgery and surgical steps. This reduces surgical costs, for example, with respect to the number of pieces of equipment to be used, with respect to the material to be used, with respect to the cleaning and sterilizing procedures to be carried out, etc.

The relatively simple construction of the front-lens attachment (without optical components, without motor-driven or manual positioning units or complicated gears and the like) is simple to clean, disinfect, and sterilize. Therefore, the entire front-lens attachment is rapid and simple to use under sterile conditions.

According to another aspect of the invention, a turret attachment is provided for the rotatable arrangement of at least two lens elements on a front-lens attachment for an optical observation device, particularly for a microscope. In particular, the turret attachment can be provided for the rotatable arrangement on a front-lens attachment according to the invention as described above, so that everything stated relative to the turret attachment also applies in connection with the front-lens attachment according to the invention. In this connection, a front-lens attachment consisting of a focussing device, a covering cap, a retaining device disposed thereon and an appropriate turret attachment is advantageous.

The turret attachment has a retaining element that can be rotated around an axis of rotation, which can be designed in the way described above, on which the at least two lens elements are disposed.

The entire turret attachment then represents a type of lens element changer, wherein the lens elements are found on the retaining element and the retaining element is mounted in a rotatable manner, so that the lens elements can be further rotated, as in the cylinder of a turret. In this case, it is particularly provided that each of the individual lens elements can be rotated into discrete positions, for example, a park position or a working position. Of course, it is also conceivable that the lens elements can be rotated up to 360 degrees.

It can be advantageously provided that the retaining element of such a turret attachment, and also the retaining element in general, as described further above, is formed as a lens uptake, that the at least two lens elements are each arranged on a lens holder and are disposed on the lens uptake by means of the holders, particularly in a detachable manner. It can advantageously be provided that at least one lens holder has a curved course or angular course or bent course, at least in regions.

Further, it is advantageous if the axis of rotation of the turret attachment relative to an optical axis of the observation device to which the turret attachment is fastened, preferably by means of a suitable front-lens attachment, has an inclined course.

By means of such a turret attachment, different lens elements, for example, ophthalmoscopic magnifying lenses, can be alternatively swung into the beam path of an optics for a short period of time, even during an operation, even several times and also under sterile conditions, or all lens elements, for example, ophthalmoscopic magnifying lenses can be swung out away from the beam path by means of an appropriate intermediate positioning. The turret attachment is configured via an appropriate configuration of the retaining element so that the respective ophthalmoscopic magnifying lens(es), which is/are not required, obstruct the structural space below the observation device as little as possible. This is particularly achieved by an appropriate angular arrangement of the rotating joints and a bending of the lens holders.

The use of such a turret attachment, which then has the function of an ophthalmoscopic magnifying lens changer, makes possible the alternate, non-simultaneous swinging in of different ophthalmoscopic magnifying lenses as well as the swinging out of (all) ophthalmoscopic magnifying lenses from the beam path of the observation device when the focussing optics are swung in, for example, when contact lenses are employed. The turret attachment and the ophthalmoscopic magnifying lenses, for example, their mounts, are thus configured in such a way that the lenses, depending on their refractive power, can be positioned at different, defined distances relative to the observation device or to the patient's eye.

According to another aspect of the invention, an optical observation device is provided, which is characterized according to the invention in that it has at least one front-lens attachment according to the invention, as described above, and/or a turret attachment according to the invention. In order to avoid repetition, reference is therefore first made to the above statements to the full extent for the front-lens attachment and turret attachment according to the invention. Advantageously, the optical observation device may involve a microscope.

According to yet another aspect of the invention, an optical observation device, particularly a microscope, is provided, which is characterized in that it has a front-lens attachment according to the invention as described above, and that in addition, a focussing device is provided, which is integrated in the optical observation device. In order to avoid repetition, reference is therefore first made also in this respect to the above statements to the full extent for the front-lens attachment according to the invention. Advantageously, the optical observation device may also have a turret attachment according to the invention, as described above, so that also in this respect, reference is made in the full extent to the corresponding statements. Advantageously, the optical observation device may involve a microscope.

The optical observation device preferably may have an objective, whereby the front-lens attachment is disposed on the optical observation device in the region surrounding the objective. Advantageously, the arrangement of the front-lens attachment can be made in the edge region of the objective. The front-lens attachment is thus arranged advantageously in such a way that the lens element can be introduced into the beam path, which passes through the objective.

It can be advantageously provided that the front-lens attachment is disposed on the optical observation device so that it can pivot and/or rotate and/or move linearly.

The front-lens attachment advantageously consists of the basic components: focussing device, covering cap, positioning device and retaining device with retaining element.

The front-lens attachment preferably can be disposed on the optical observation device in a detachable manner. In this way, the front-lens attachment can be easily removed and, for example, subjected to a cleaning, a sterilization in an autoclave or similar procedure.

It is preferably provided that the focussing device is disposed on the optical observation device for a long period of time. For example, the focussing device can be fastened onto the microscope by means of an adapter, e.g., a bayonet-dovetail guide piece, for a long period of time, i.e., over the duration of a surgical intervention. It can also be removed in this way as needed via this adapter/coupling site between individual surgical interventions, in particular under non-sterile conditions. After placing/plugging in the front-lens attachment or the focussing device on the adapter, the latter is secured/fixed against undesired loosening during operations by means of a suitable fixation, for example a catch or locking and/or clamping mechanism. The fact that the front-lens attachment or the focussing device can be detached from the optical observation device, for example, from the microscope, is then particularly of advantage when the latter is used not for fundus surgeries, but exclusively for surgeries of the front segment [of the eye] over a long period of time or for several surgeries, particularly relative to more working space, lower weight, fewer disruptive contours and similar considerations. Since the focussing device can be detached from the optical observation device, a reduction of disruptive contours in surgeries of the front segment is made possible.

The focussing device is usually a complicated construction and is very sensitive. Therefore, it is usually not cleaned and sterilized. For this purpose, there is present the at least one covering cap, which in its turn, can be cleaned and sterilized, and which is joined in a detachable manner with the focussing device and covers it. The use of the covering cap with the retaining device disposed thereon then makes possible a sterile operation.

For example, it can be provided that the front-lens attachment or the focussing device is disposed on the optical observation device so that it can move. This can be accomplished, for example, by means of a sliding mechanism, e.g., a linear guide. The guide advantageously can have two locking end positions. The focussing/reducing optics can be swung into the beam path of the observation device as well as swung out from the beam path temporarily, in fact several times during the surgical intervention and this can be conducted in such a way that there are minimal constrictions of the working space, which leads to a configuration that is minimized in its structural space. The covering cap attached to the movable region of the focussing device moves along with such movement of swinging in and out. A swinging out is particularly meaningful/necessary for working on the front segment, in particular in order to avoid undesired reflections and the like due to the partly complex illumination of the microscope. In addition, the working space directly under the principal objective of the microscope is freed up, which leads to a reduction of disruptive contours, to more freedom of movement, etc.

Advantageously, the optical observation device can be designed as an operating microscope, in particular as an operating microscope for ophthalmology.

A front-lens attachment according to the invention as described above and/or an optical observation device according to the invention as described above can advantageously be used for indirect contact-free ophthalmology or indirect ophthalmology with contact.

The optical observation device, for example, an operating microscope, may also contain a system for transposing the beam and for inverting the image, which system is advantageously located in the binocular tube piece.

BRIEF DESCRIPTION OF THE DRAWINGS

The invention will now be explained in more detail on the basis of embodiment examples with reference to the appended drawings. Here.

FIG. 22 shows a first working position of the optical observation device relative to a patient to be operated on;

FIG. 23 shows a second working position of the optical observation device relative to a patient to be operated on;

FIG. 24 shows a third working position of the optical observation device relative to a patient to be operated on; and FIG. 25 shows a fourth working position of the optical observation device relative to a patient to be operated on.

DETAILED DESCRIPTION OF THE INVENTION

An optical observation device 10 in the form of an operating microscope for ophthalmology, which is known in and of itself, is shown in the figures. Operating microscope 10 shall involve an ophthalmoscopic microscope.

Such microscopes are known in and of themselves to the person skilled in the art, so that in the present case, their basic structure will not be dealt with further.

Figure 1:
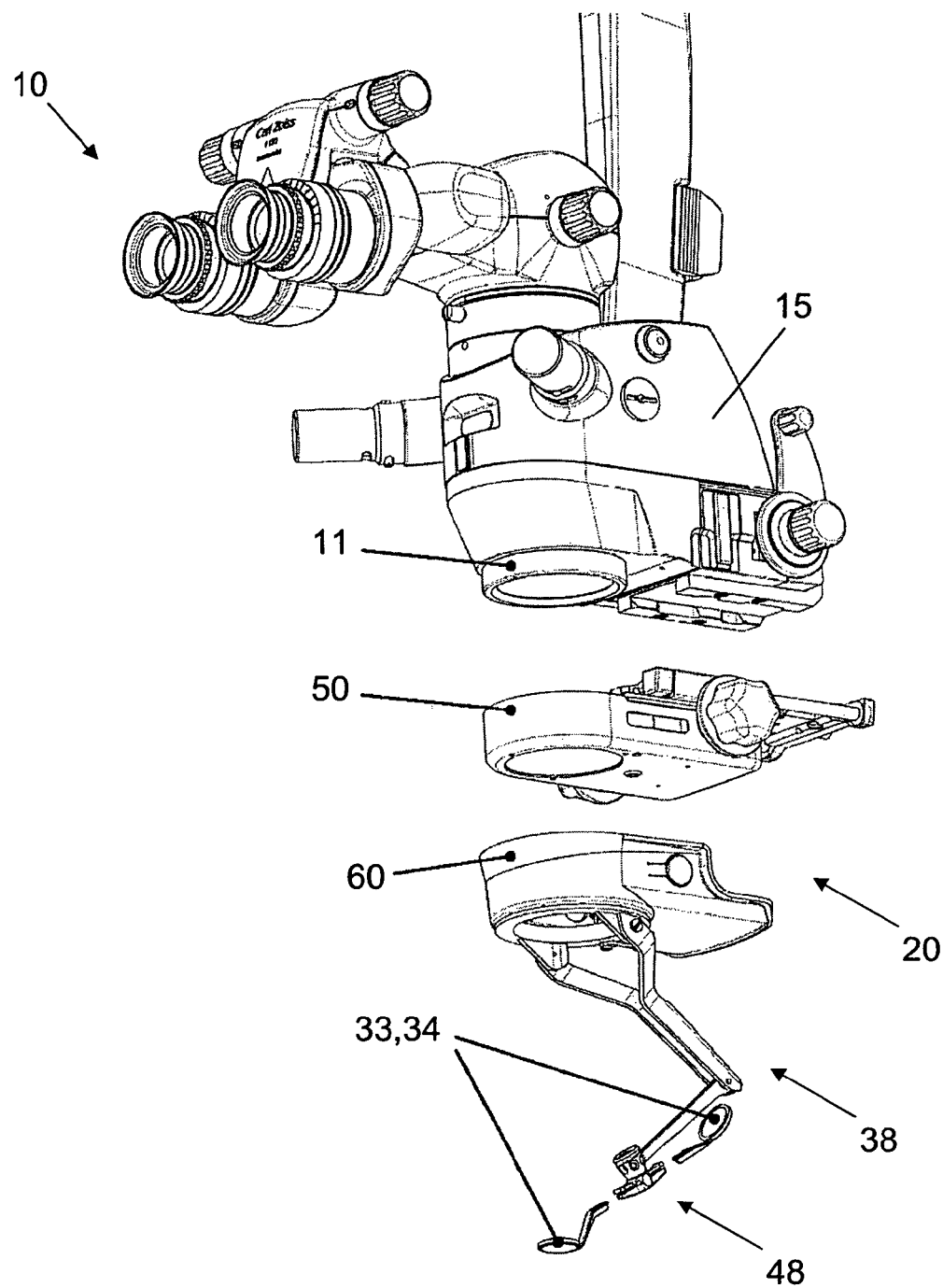
FIG. 1 is an exploded view of an optical observation device according to the invention in the form of an operating microscope.
Figure 2:
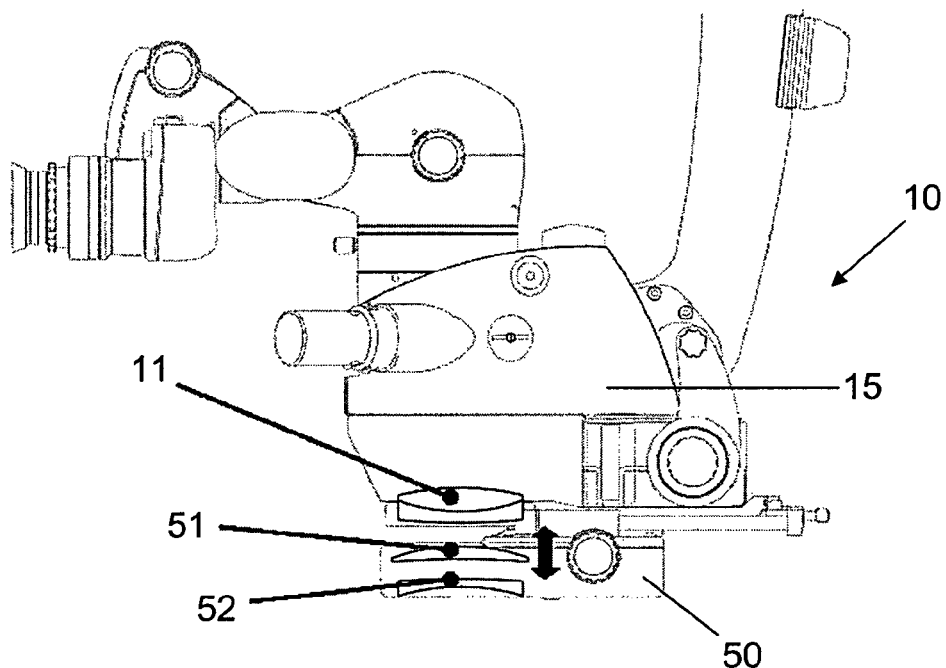
FIG. 2 is a side view of the optical observation device with attached focussing device.

As is first illustrated in FIG. 1, microscope 10 is comprised of a microscope body 15, which has an objective 11. Here, this involves the principal objective of microscope 10. A focussing device 50, which will be further detailed below, is disposed on the underside of microscope body 15. A covering cap 60 is attached to focussing device 50, which represents one component of a front-lens attachment 20. In turn, a retaining device 38, by means of which lens elements 33, 34 are held, is attached to covering cap 60. Lens elements 33, 34 are attached to retaining device 38 in a rotatable manner via a turret attachment 48. The turret attachment 48 is explained in more detail below in connection with FIGS. 11 and 20.

Figure 3:
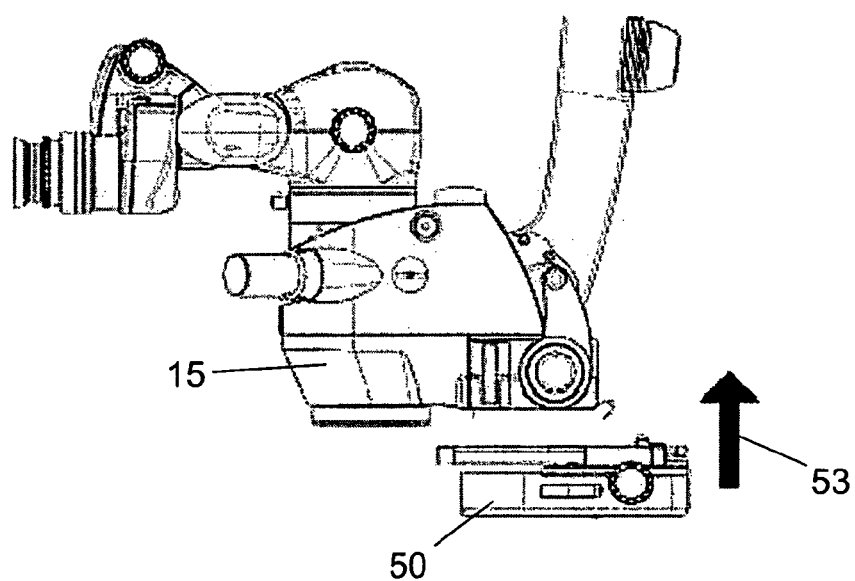
FIG. 3 is the representation shown in FIG. 2, at the beginning of the attachment of the focussing device.
Figure 4:
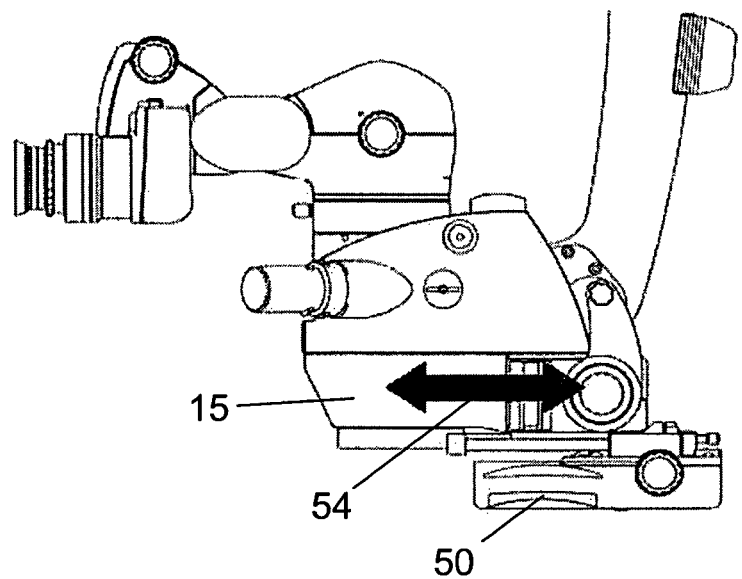
FIG. 4 is the representation shown in FIG. 2, in which the focussing device is found in a first shifted position.
Figure 5:
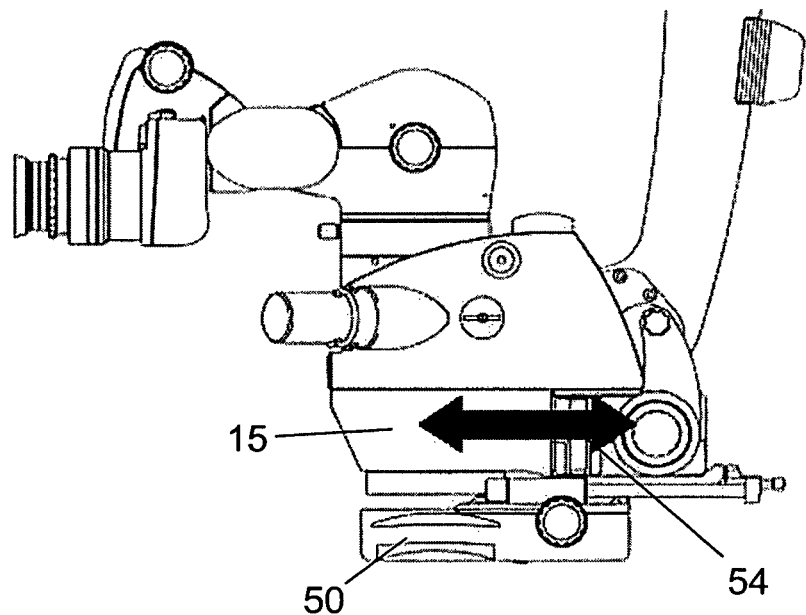
FIG. 5 is the representation shown in FIG. 2, in which the focussing device is found in a second shifted position.

The fastening as well as the positioning with respect to a swinging in and out of focussing device 50 on microscope body 15 is described below on the basis of FIGS. 2 to 5. It is first shown (FIG. 2) that the focussing device 50 is designed in the form of a focussing optics, for example, a reducing optics. Focussing device 50 has two optical components in the form of a movable positive component 51 and a negative component 52 which is fixed in position. The optical components 51, 52 lie with principal objective 11 of microscope 10 on an optical axis. The optical components 51, 52 of focussing device 50 serve for focussing microscope 10 onto the intermediate image of lens elements 33, 34 (FIG. 1). FIG. 3 shows how focussing device 50 is first brought up against microscope body 15 for fastening to the microscope. This is characterized by arrow 53. After it has been fastened, it can next be achieved by means of a sliding mechanism, a so-called linear guide that has two locking end positions, that the focussing device 50 can be swung into the beam path of microscope 10 as well as swung out from the beam path temporarily, in fact several times during a surgical intervention. This displacement is characterized in FIGS. 4 and 5 by arrow 54, whereby focussing device 50 is shown in the swung-out state in FIG. 4, and focussing device 50 is shown in the swung-in state in FIG. 5.

Operating microscope 10 provides a particularly designed front-lens attachment 20 according to the invention. This front-lens attachment 20 according to the invention is characterized as excerpt A in FIG. 6. Excerpt A is shown enlarged in FIG. 7. The structure and function of the front-lens attachment 20 according to the invention will first be explained below in connection with FIG. 7.

Front-lens attachment 20 shall serve as a front lens piece for an objective 11 of operating microscope 10. For this purpose, front-lens attachment 20 is connected to operating microscope 10 in a region of the operating microscope which points toward the object region.

Front-lens attachment 20 first provides two lens elements 33, 34, in the form of ophthalmoscopic magnifying lenses. These are disposed on a positioning device 21 by means of a retaining element 32. Retaining element 32 and positioning device 21 are components of a retaining device 38.

Positioning device 21 represents an essential feature of front-lens attachment 20. Positioning device 21 generally consists of two positioning components 22, 28, which are joined together by means of a joint 31, for example, a rotating joint.

In the present example, first of all, a first positioning component 22 is provided, which has two legs 23, 24 which are distanced from one another and which bound an uptake space 25. On one end 26 of first positioning component 22, it is joined with the second positioning component 28 via joint 31.

The second end 27 of the first positioning component 22 serves for fastening the retaining device 38 to a covering cap 60 of the front-lens attachment 20. Covering cap 60 serves for the purpose of covering focussing device 50 (not shown in FIG. 7) in a sterile manner. Covering cap 60 is advantageously disposed on focussing device 50 in a detachable manner. In this way, covering cap 50* plus retaining device 38 can be removed from microscope 10 and can be comfortably cleaned, disinfected and sterilized after terminating the operation.

*sic; 60?—Trans. Note.

Retaining device 38 can be attached to covering cap 60 by means of a suitable fastening means 35 with rotating joint, for example, an appropriately designed bolt or screw connection. For this purpose, fastening means 35 cooperate with corresponding fastening legs 13, 14, which are formed in a fastening region 12 on covering cap 60. By means of this fastening, retaining device 38 with first positioning component 22 is disposed on covering cap 60 of front-lens attachment 20 so that it can pivot in a first pivoting direction. In this way, it can be provided that the front-lens attachment 20 is disposed in a detachable manner on operating microscope 10. Therefore, it can be easily removed for cleaning and sterilizing purposes and can be introduced, for example, into an autoclave.

The second positioning component 28 is designed in the form of a rod and is joined with the first positioning component 22 on one of its ends 29 by means of joint 31. Joint 31 is thus designed in such a way that the two positioning components 22, 28 can be folded up. This is carried out in such a way that the second positioning component 28, when in the folded-up state, comes to lie within the uptake space 25 of the first positioning component 22.

Retaining element 32 is disposed so that it can rotate on the other end 30 of the second positioning component 28. Retaining element 32 is thus formed as a retaining arm, whereby retaining arm 32 has two arm regions, each of which projects from the central position, on which retaining arm 32 is joined with end 30 of positioning component 28. The lens elements 33, 34 are provided on each of the outer ends of retaining arm 32.

Retaining arm 32, and with it, lens elements 33, 34, can be pivoted via the second positioning component 28 and joint 31 into a second pivoting direction 37 that differs from first pivoting direction 36.

Figure 6:
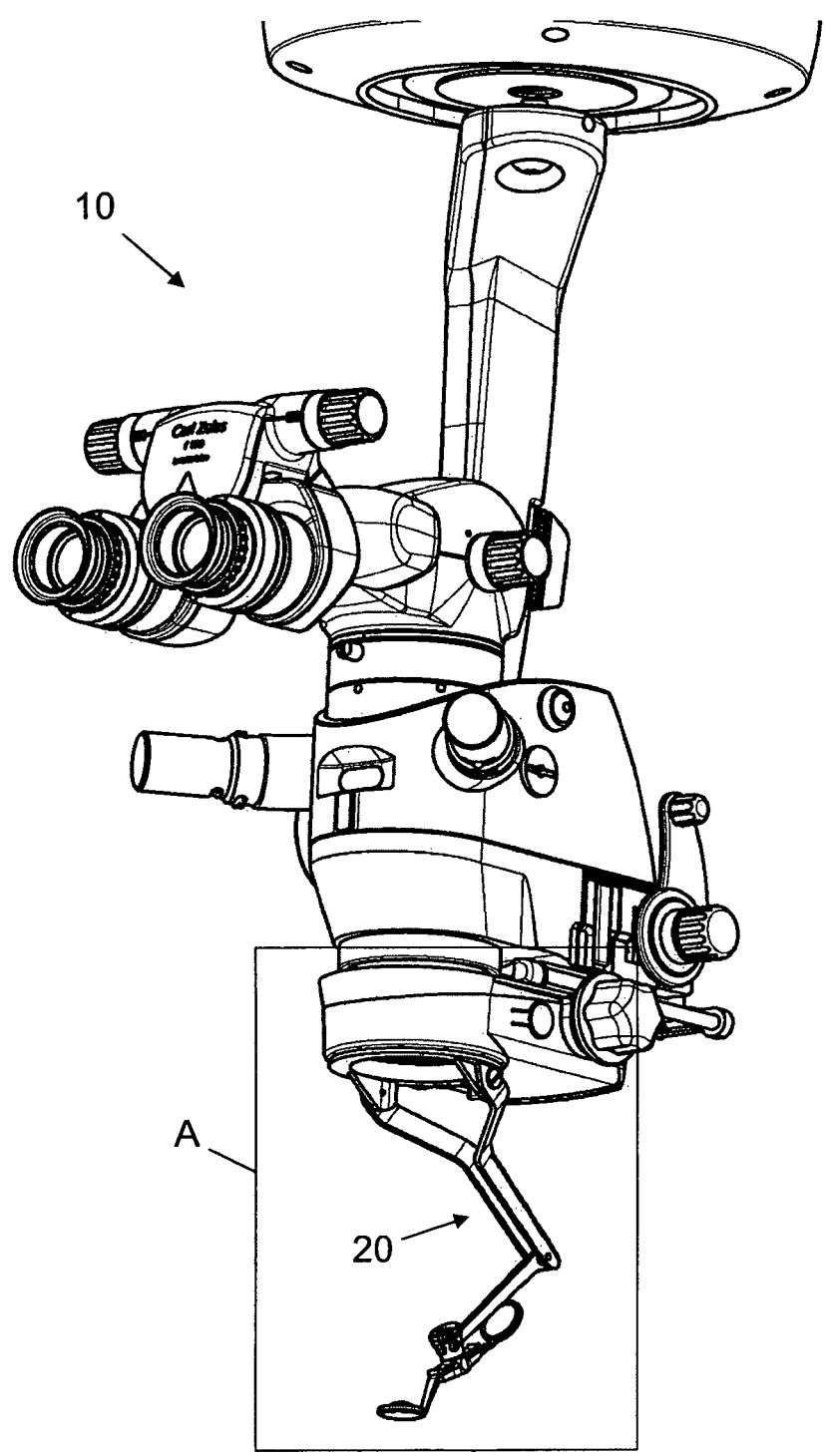
FIG. 6 is a perspective view of an optical observation device with the front-lens attachment according to the invention, wherein the front-lens attachment is found in the spread-apart state.
Figure 7:
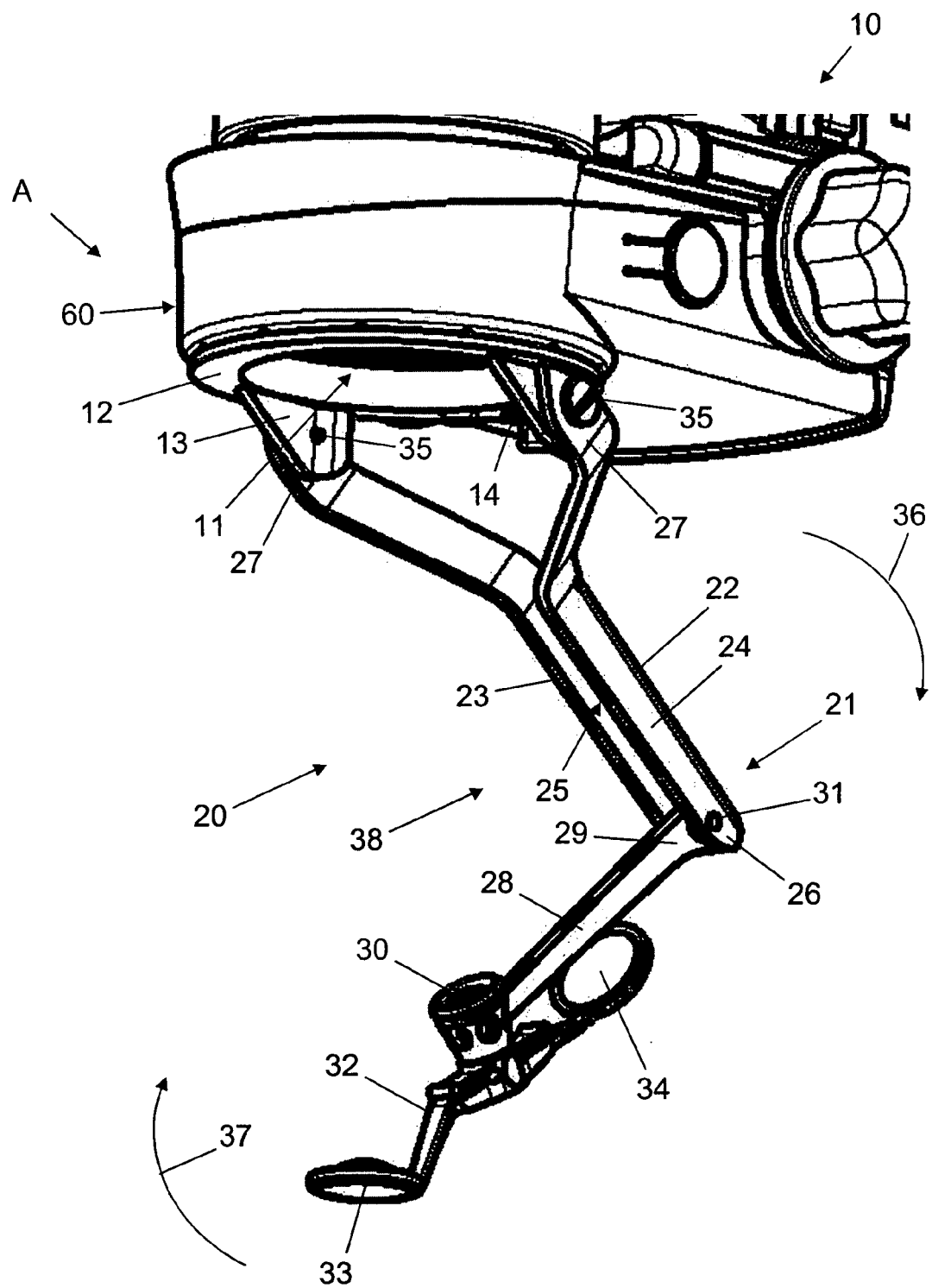
FIG. 7 is excerpt A shown in FIG. 6 in increased magnification.
Figure 12:
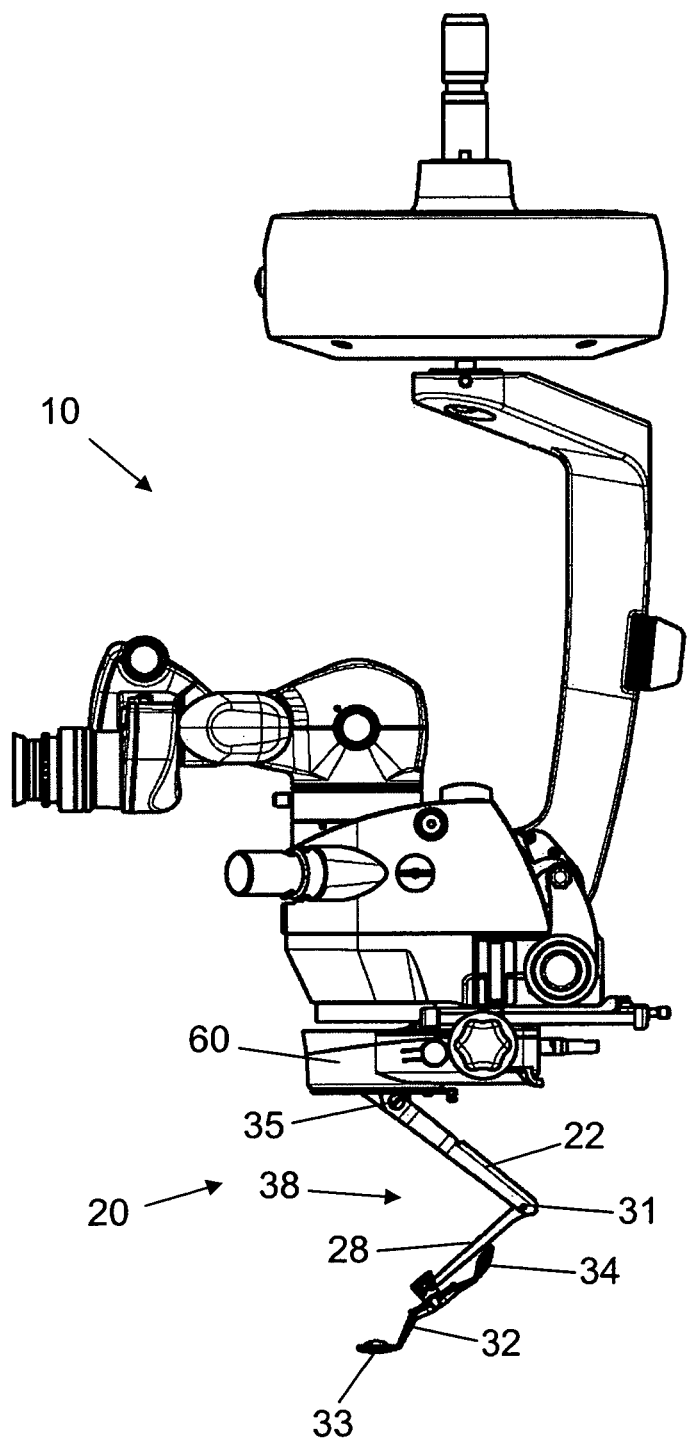
FIG. 12 is a lateral view of the optical observation device shown in FIG. 6.

A first state is shown in FIGS. 6, 7 and 12, in which front-lens attachment 20 is completely spread apart. This spread-apart position can be taken, for example, based on gravitational force. If, e.g., a respective attachment is loosened, the front-lens attachment alone falls into the spread-apart position based on gravitational force. By means of an appropriate rotation of retaining arm 32, it is possible for the surgeon to introduce the first lens element 33 or the second lens element 34, as desired, into a beam path which runs through objective 11, or to swing both lens elements out from the beam path.

Figure 13:
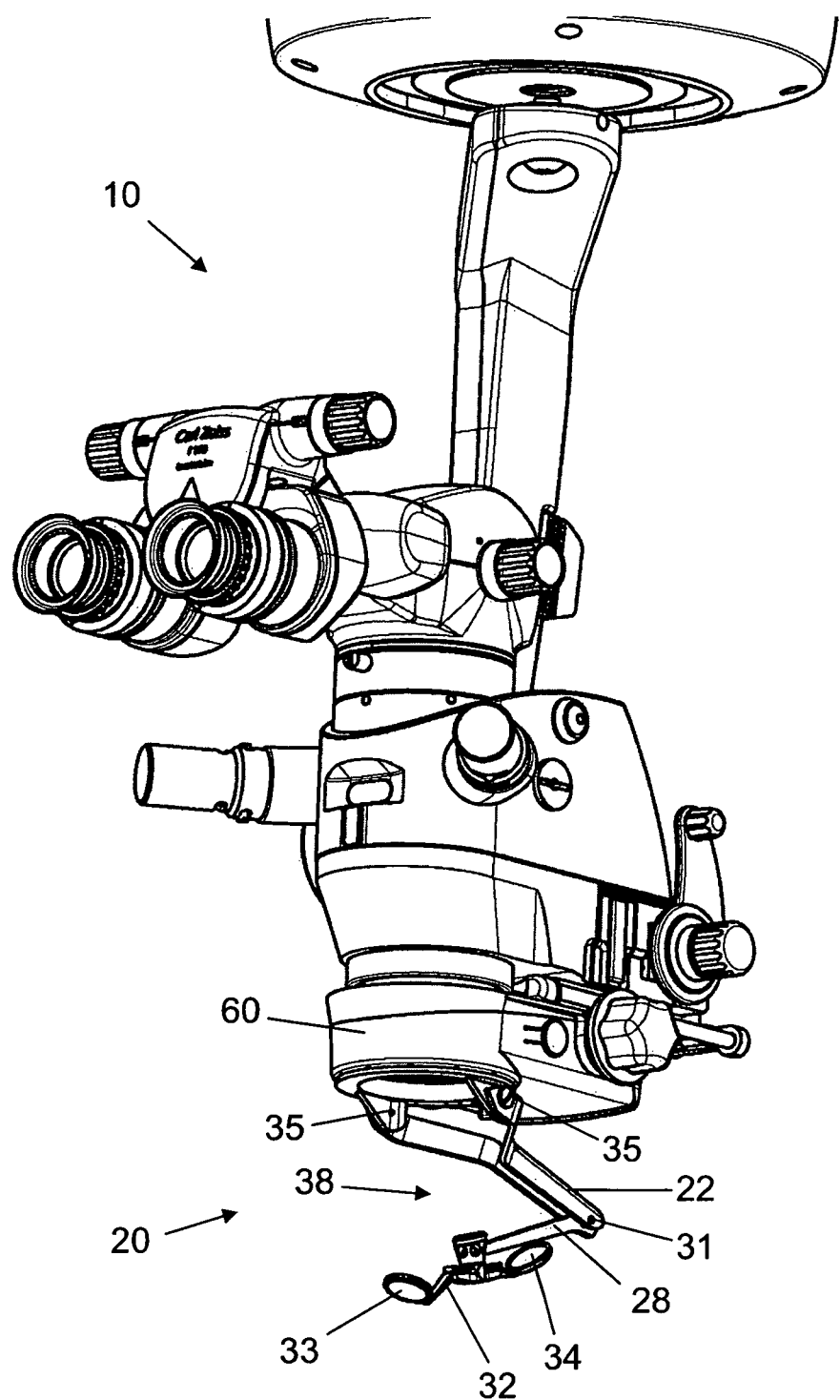
FIG. 13 is a perspective view of an optical observation device with a front-lens attachment according to the invention, wherein the latter is brought from a previously spread-apart state into a folded-up state.
Figure 14:
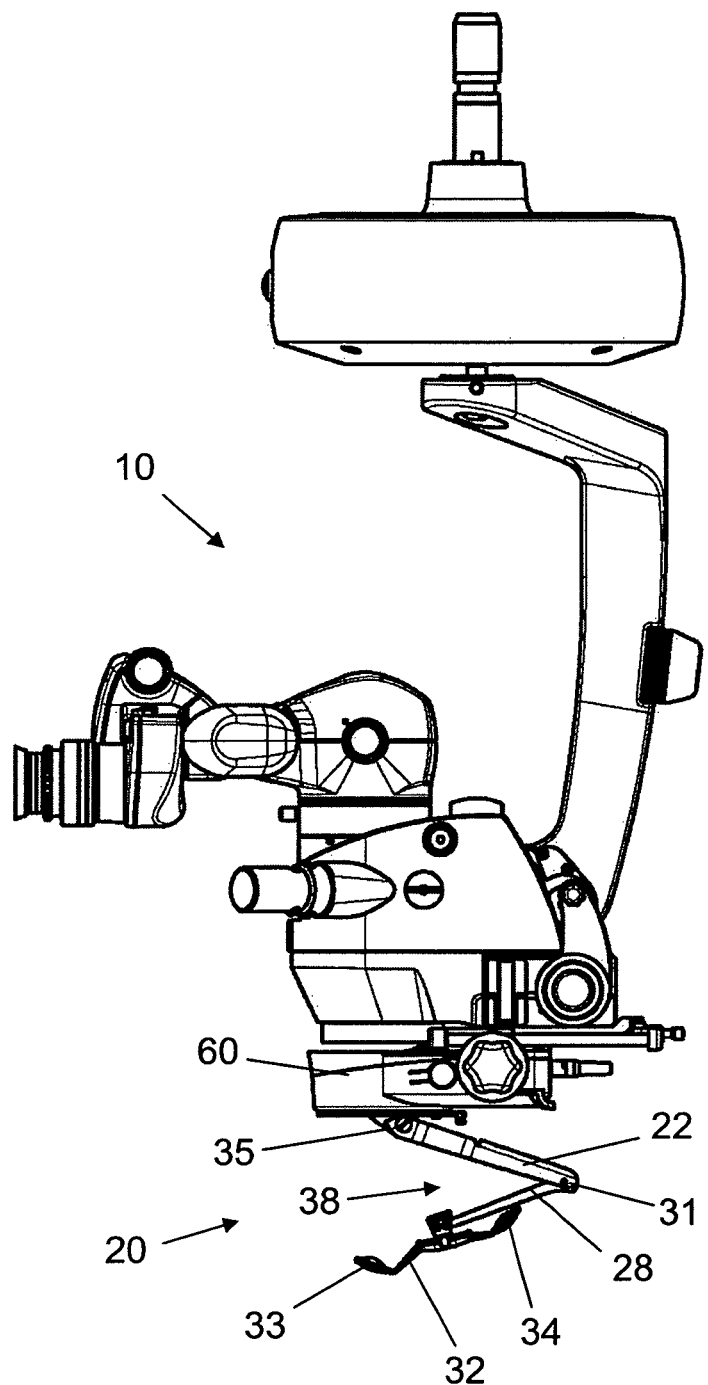
FIG. 14 is a lateral view of the optical observation device shown in FIG. 13.

A second state is shown in FIGS. 13 and 14, in which front-lens attachment 20 is partly folded up. In this case, this is not a working position in the example of embodiment. Rather, an intermediate position is shown in the named figures, which illustrates the mobility of positioning device 21 based on a gravitational mechanism.

Figure 15:
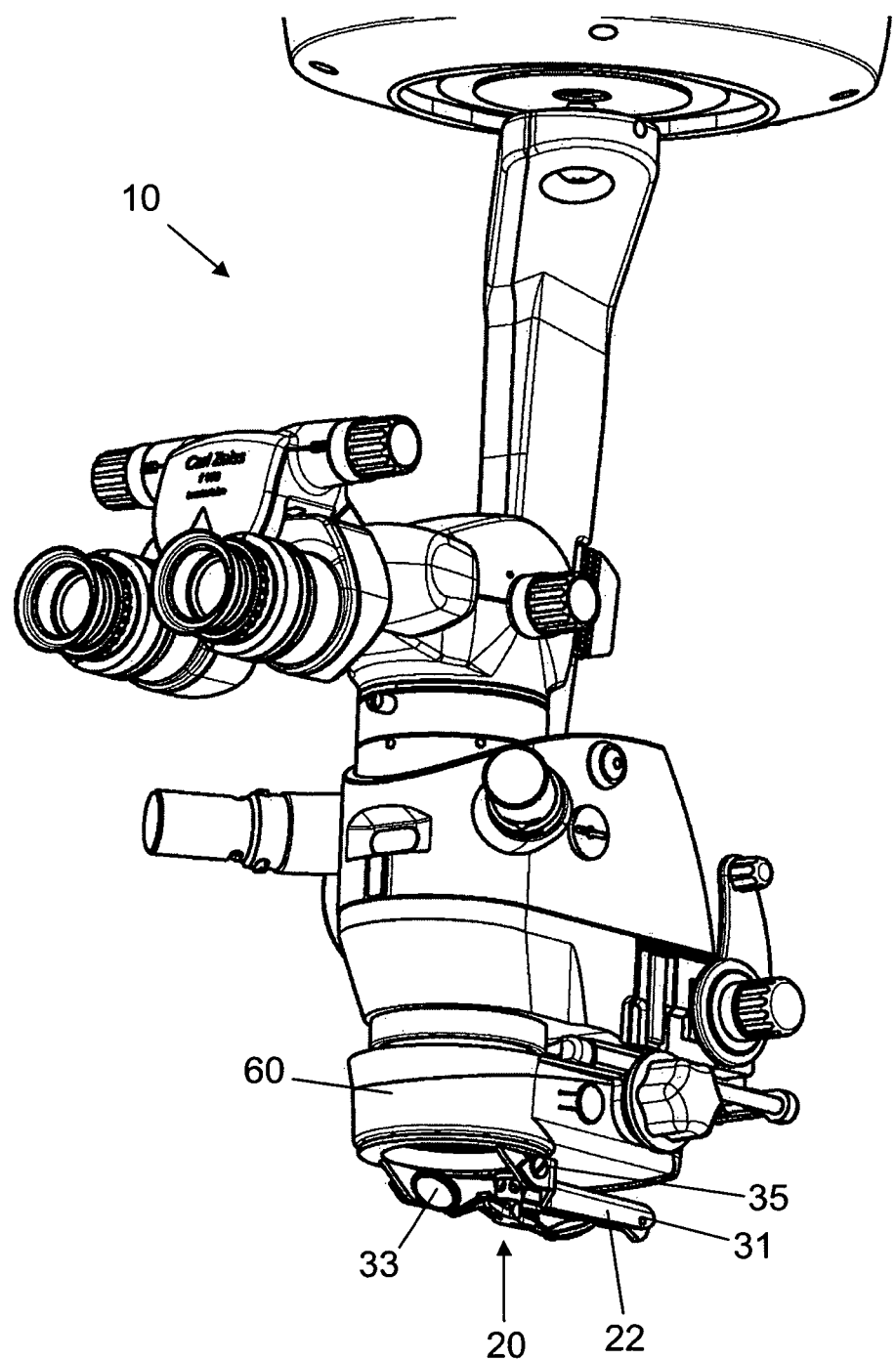
FIG. 15 is a perspective view of an optical observation device with the front-lens attachment according to the invention, whereby the latter is found in a folded-up state.
Figure 16:
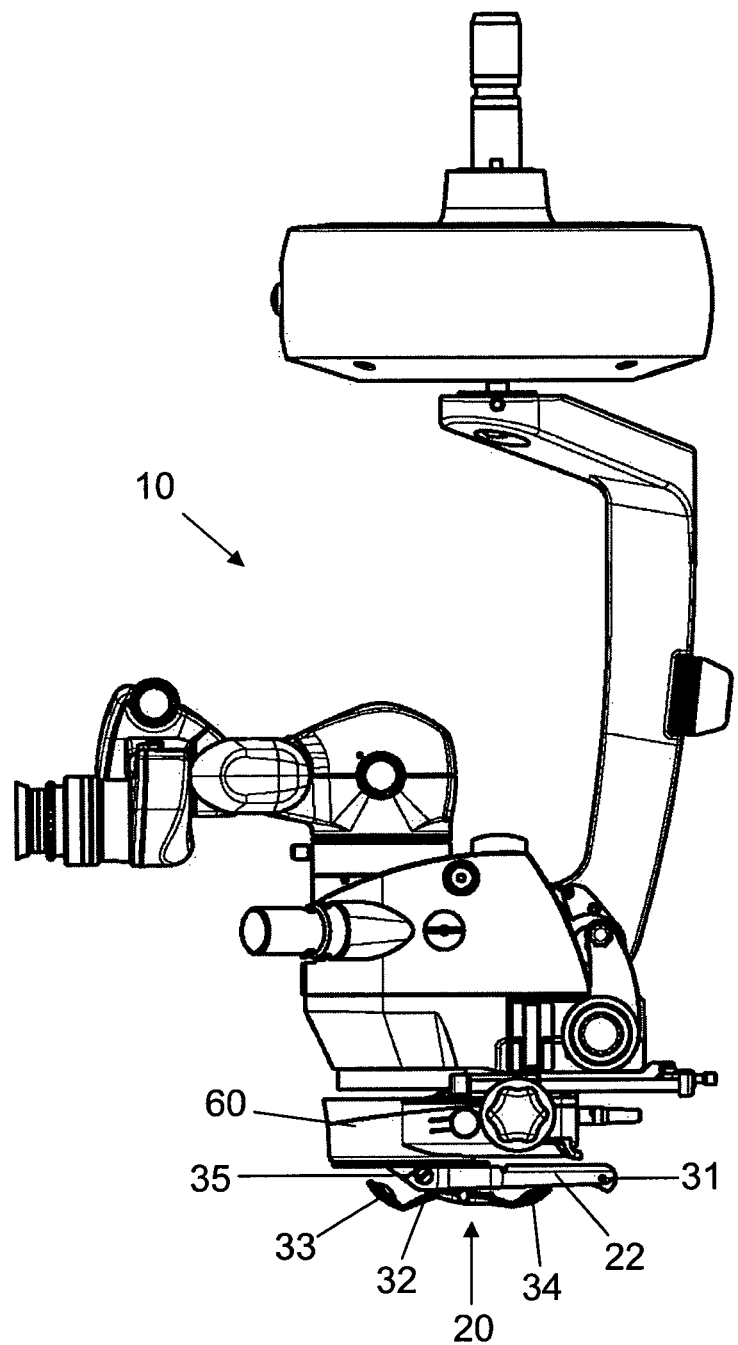
FIG. 16 is a lateral view of the optical observation device shown in FIG. 15.
Figure 17:
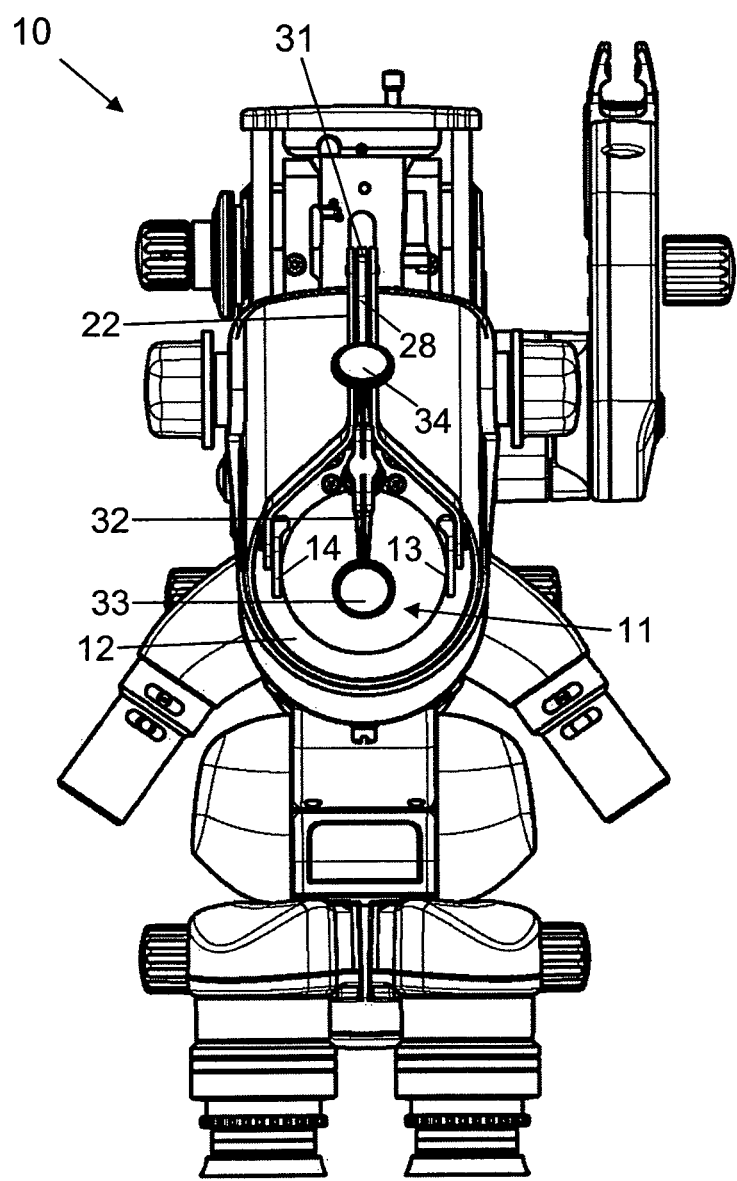
FIG. 17 is a view from below onto the optical observation device shown in FIGS. 15 and 16 with a folded-up front-lens attachment.
Figure 18:
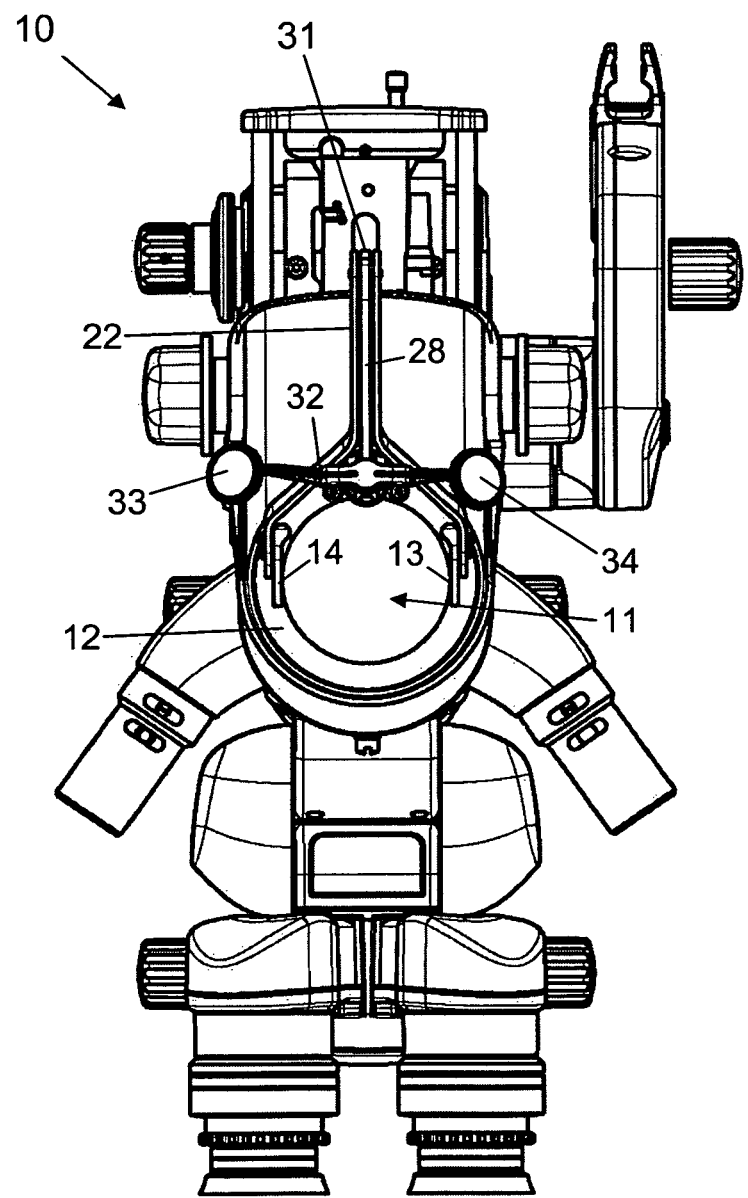
FIG. 18 is a view according to FIG. 17, in which the folded-up front-lens attachment is found in a park position.
Figure 19:
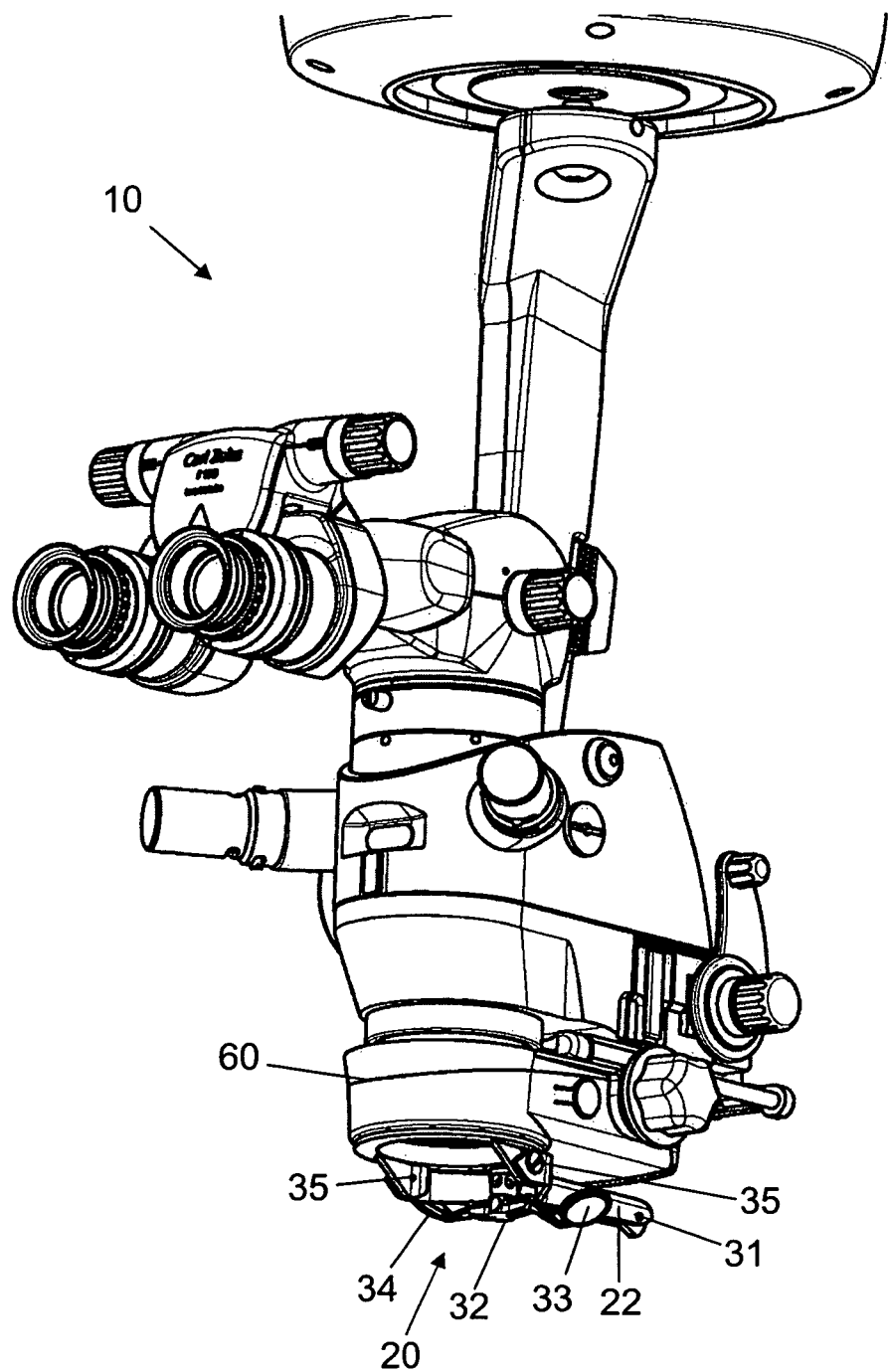
FIG. 19 is a perspective view onto the optical observation device shown in FIG. 18, whereby the latter is found in a folded-up state and in a park position.

Finally, front-lens attachment 20 is shown in the folded-up state in FIGS. 15 to 19. First of all, it is clear that it can be achieved by an angular course of retaining arm 32, at least in part, that lens elements 33, 34, or at least the lens element that is not necessary at the moment, lies/lie very close to operating microscope 10, so that they/it do/does not interfere with the surgeon during operation. A situation is shown in FIGS. 15, 16 and 17, in which lens element 33 is found in the beam path. A situation is shown, however, in FIGS. 18 and 19, in which lens elements 33, 34 are found in a type of park position, in which no lens element is found in the beam path. Such a park position is advantageous, for example, if a contact lens shall be used, which is applied directly to the patient's eye, so that lens elements 33, 34 are not necessary. In such a case, however, it is always advantageous if focussing device 50 is active, in order to make it possible to work with a contact lens.

Figure 8:
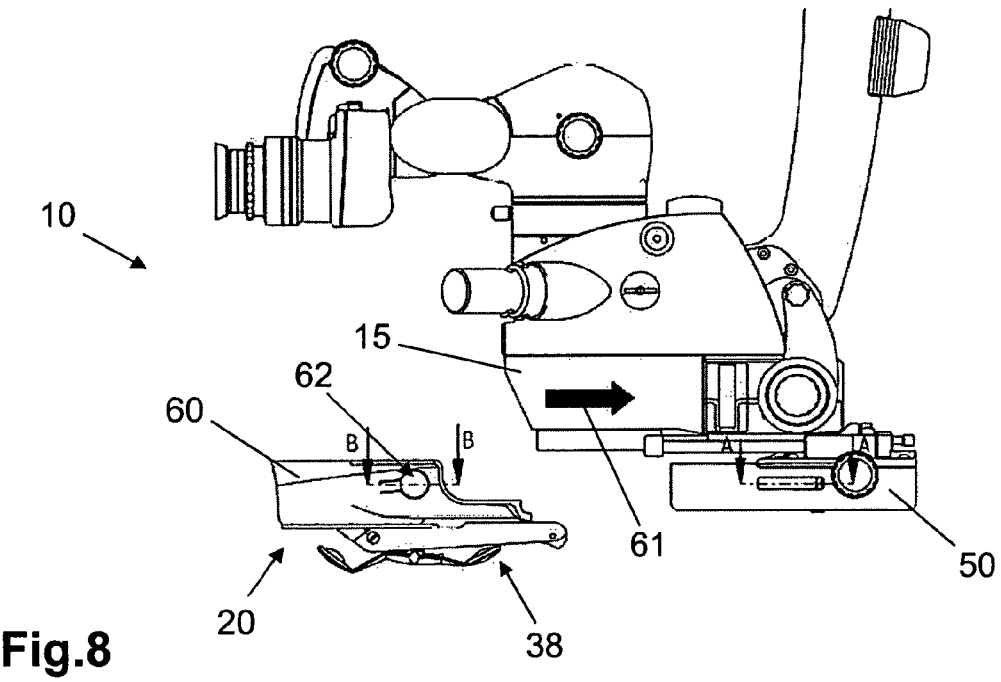
FIG. 8 is a side representation of an optical observation device, just before attaching the covering cap to the focussing device.
Figure 9:
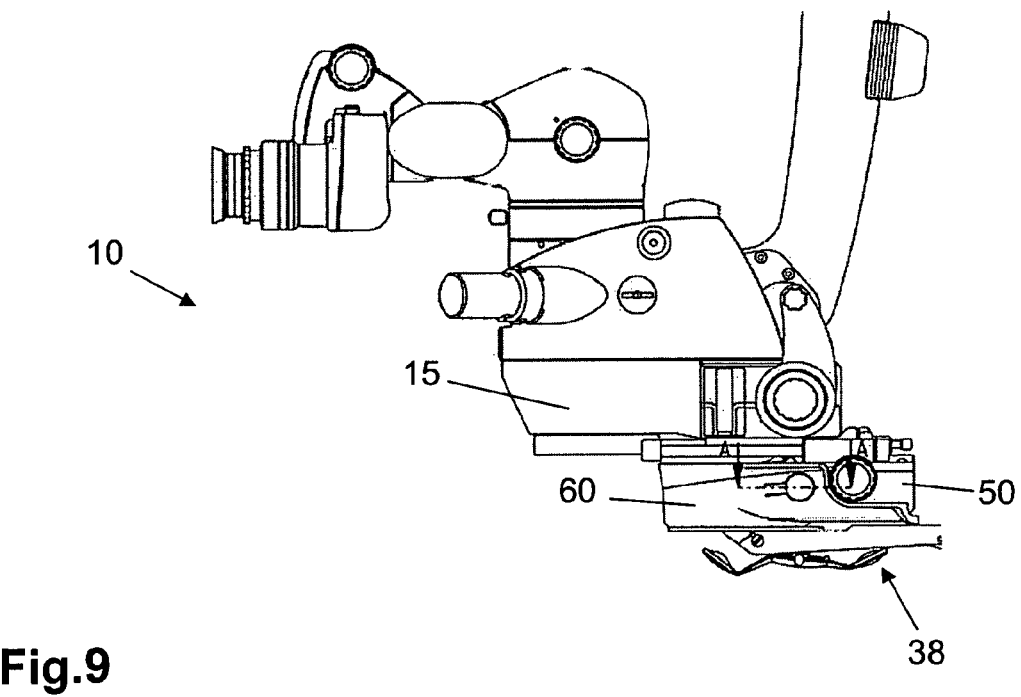
FIG. 9 is the representation shown in FIG. 8 after complete attachment of the covering cap to the focussing device.
Figure 10:
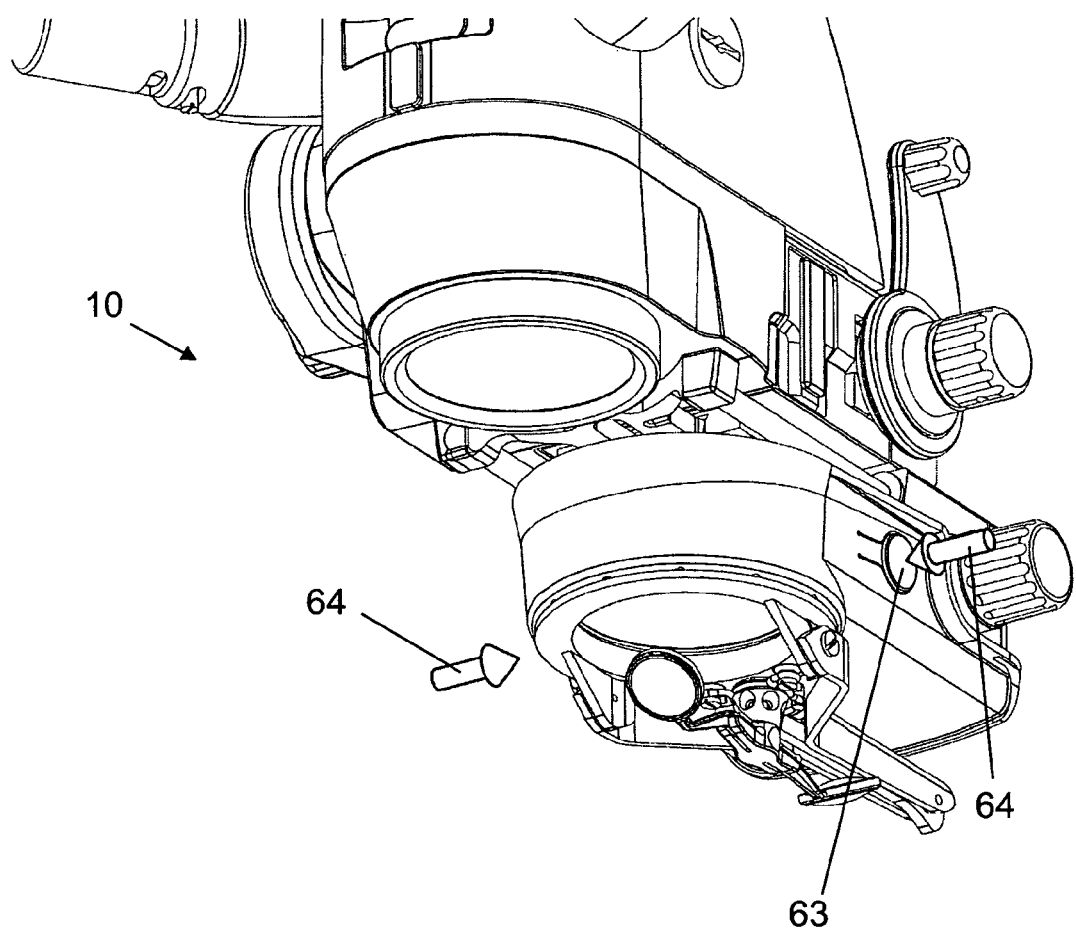
FIG. 10 is one possibility for unlocking the covering cap for detachment of the same from the focussing device.

It is shown in FIGS. 8 to 10 how front-lens attachment 20 is attached to microscope body 15 of microscope 10 via covering cap 60, on which is found retaining device 38.

The sterile covering cap 60 can be temporarily placed on the movable region of focussing device 50—also under sterile conditions during surgery (and even repeatedly as needed). The direction of placement is characterized by arrow 61. As can be seen in FIG. 8, covering cap 60 is plugged onto focussing device 50 from the front. When it has been plugged in place, cap 60 is locked, so that covering cap 60 is aligned toward focussing device 50 and is secured against undesired loosening during surgery. Fixing is carried out by means of a fixing device 62, in which catch pieces or locking pieces can engage in an undercut. The catch pieces can be held in this fixing position by means of a spring loading. Covering cap 60 is shown in FIG. 9 in its plugged-on state. Covering cap 60 can be unlocked or loosened by means of two control elements/unlocking buttons 63 on covering cap 60. By pressing on buttons 63 in the unlocking direction 64 (FIG. 10), the catch piece is removed from the back engagement, whereupon covering cap 60 is detached from fixing* device 50 and can be removed from the latter.

Figure 11:
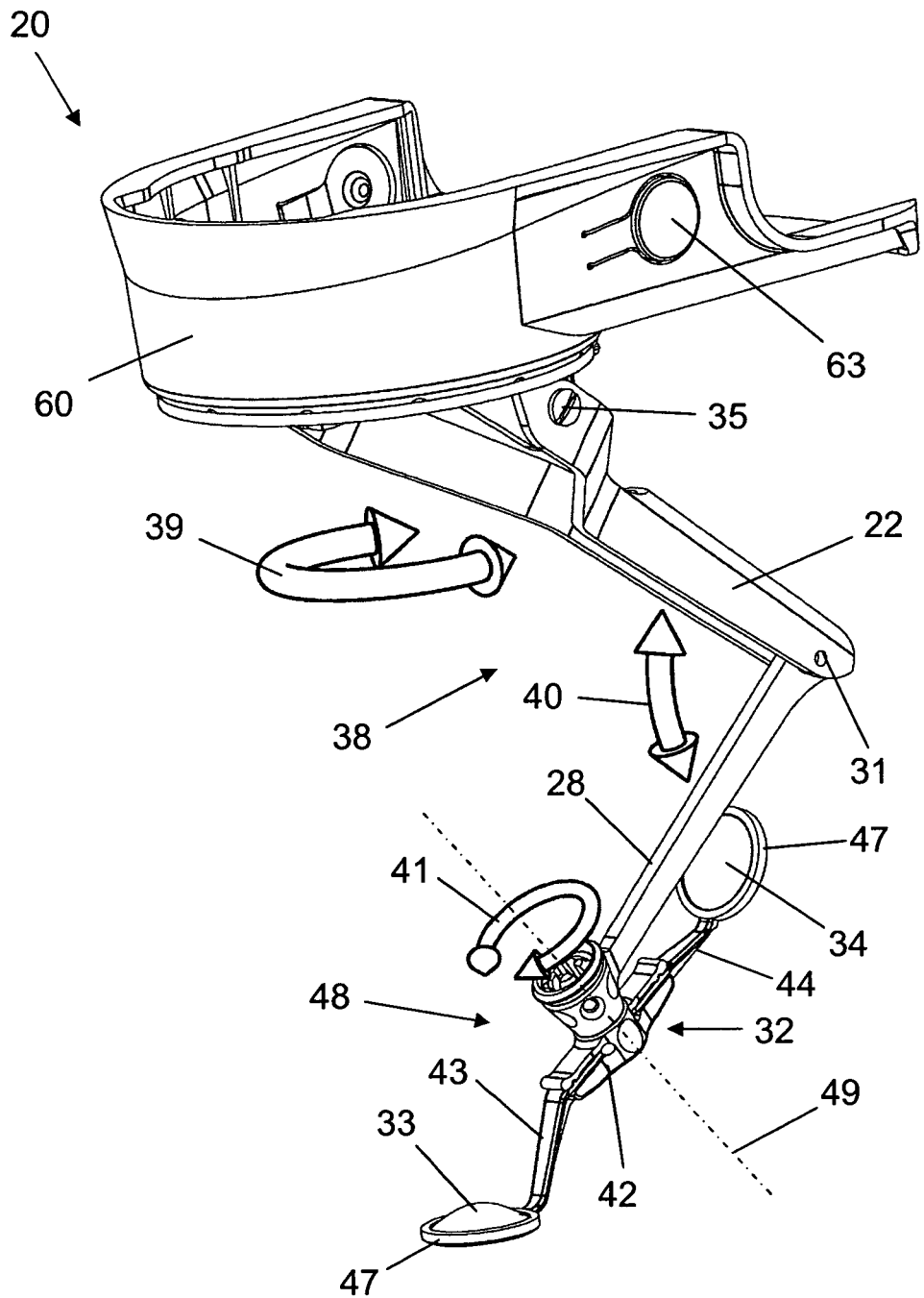
FIG. 11 is an overview of the functions of the front-lens attachment.

FIG. 11 shows an overview of the different functions of front-lens attachment 20. Front-lens attachment 20 is designed so that covering cap 60 is first of all fastened to focussing device 50 in a detachable manner. Detaching can be carried out by pressing unlocking buttons 63. By means of first positioning component 22 and fastening means 35, retaining device 38 is fastened onto covering cap 60. In this way, it can be provided that retaining device 38 is disposed in a turnable or rotatable manner on covering cap 60, which is shown by the rotating arrow 39. In addition, the two positioning components 22, 28 can be folded up and spread apart by means of rotating joint 31, which is illustrated by arrow 40, which illustrates the angle of aperture between the two positioning components 22, 28. Lens elements 33, 34 can be disposed in a turnable or rotatable manner on second positioning component 28 by means of retaining arm 32, which is characterized by arrow 41.

FIG. 11 also shows in greater detail the above-named turret attachment 48. The latter first comprises a retaining element 32, which is designed in the form of a lens uptake 42. This lens uptake 42 is disposed so that it can rotate around an axis of rotation 49 on the end of the second positioning component 28. In this case, it is provided that the axis of rotation 49 is inclined relative to the optical axis of the microscope. Turret attachment 48 makes possible a rotation of lens elements 33, 34 around the axis of rotation 41. For this purpose, lens elements 33, 34, which are held in appropriate lens mounts 47, are fastened via these mounts to bent lens holders 43, 44. Lens holders 43, 44, in turn, are fastened to lens uptake 42, preferably in a detachable manner.

Figure 20:
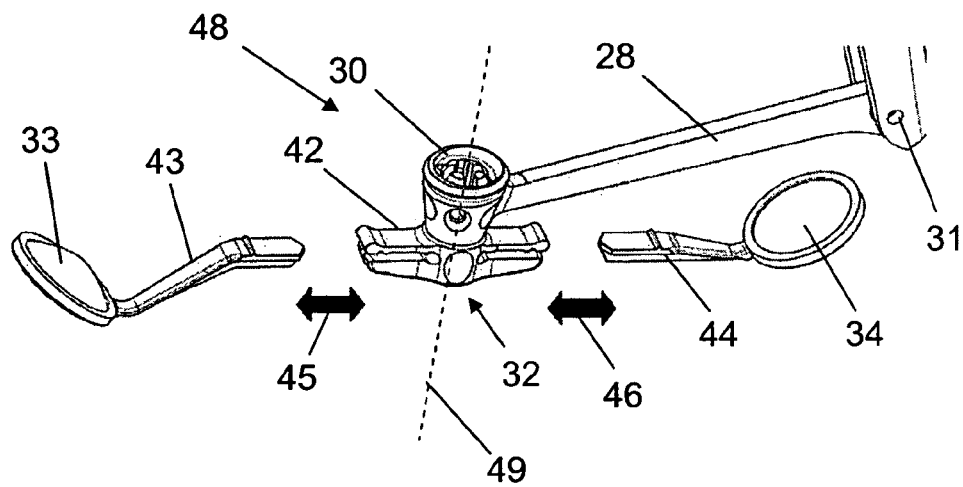
FIG. 20 is a detailed view of a retaining element for the uptake of the lens elements.

Another illustrative example for retaining element 32 is described in more detail in connection with FIG. 20. Retaining element 32 first provides a lens uptake 42, which is mounted in a turnable or rotatable manner on the free end 30 of the second positioning component 28. Positioning component 28 in turn is connected with the first positioning component via rotating joint 31. Lens holders 43, 44, on which are found lens elements 33, 34, can be plugged into lens uptake 42. The directions of insertion are characterized by the arrows 45 and 46. This plug-in connection has the advantage that the lens elements can be removed from the lens uptake 42 in a simple way, for example, for cleaning purposes and the like.

Figure 21:
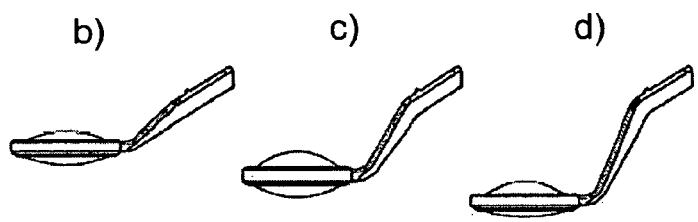
FIG. 21 shows several detailed views of different configurations of lens elements.
Figure 21:
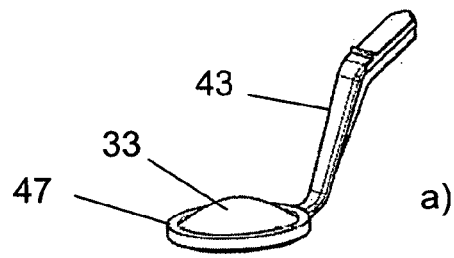

FIG. 21 shows different configurations of lens elements that involve ophthalmoscopic magnifying lenses. The actual lens element 33 is found in a lens mount 47 and is attached to lens holder 43 by the mount (FIG. 21*a*). FIG. 21*b* shows an ophthalmoscopic magnifying lens with little refractive power, FIG. 21*c* shows an ophthalmoscopic magnifying lens with medium refractive power, and FIG. 21*d* shows an ophthalmoscopic magnifying lens with high refractive power.

FIG. 21 shows lens holder 43 with bends of different types. These different types of bends are based on different optimal working distances between the ophthalmoscopic magnifying lens and the patient's eye.

FIGS. 22 to 25 finally show different typical working situations.

Figure 22:
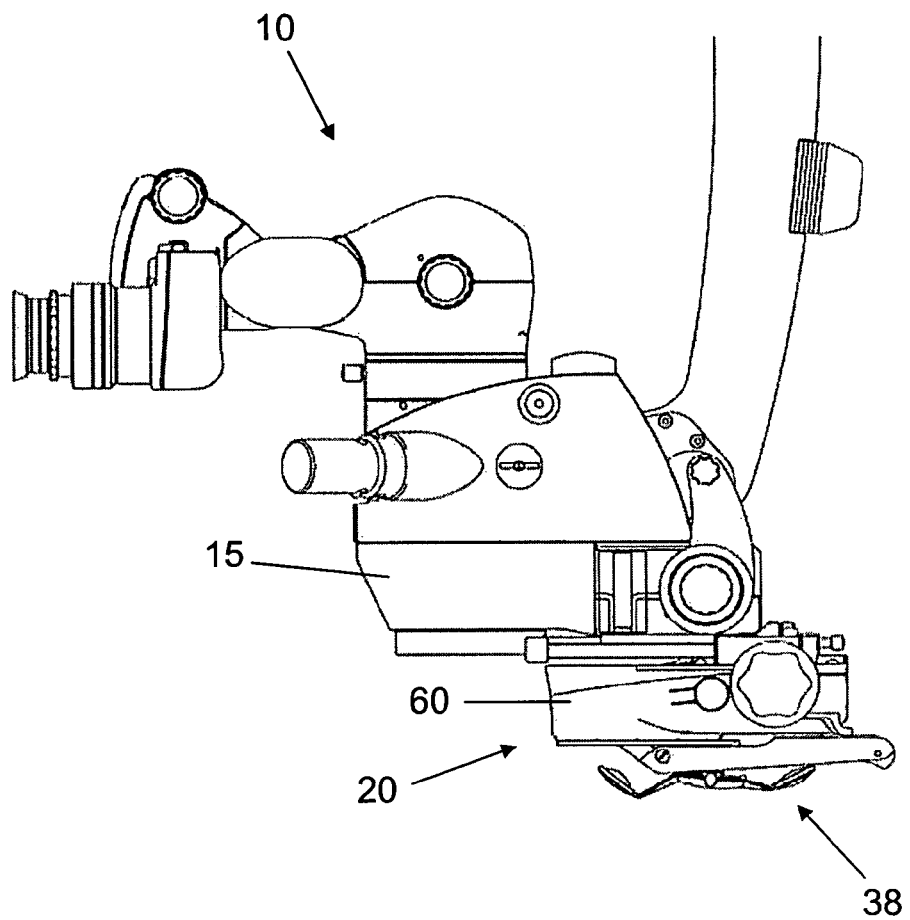
Figure 23:
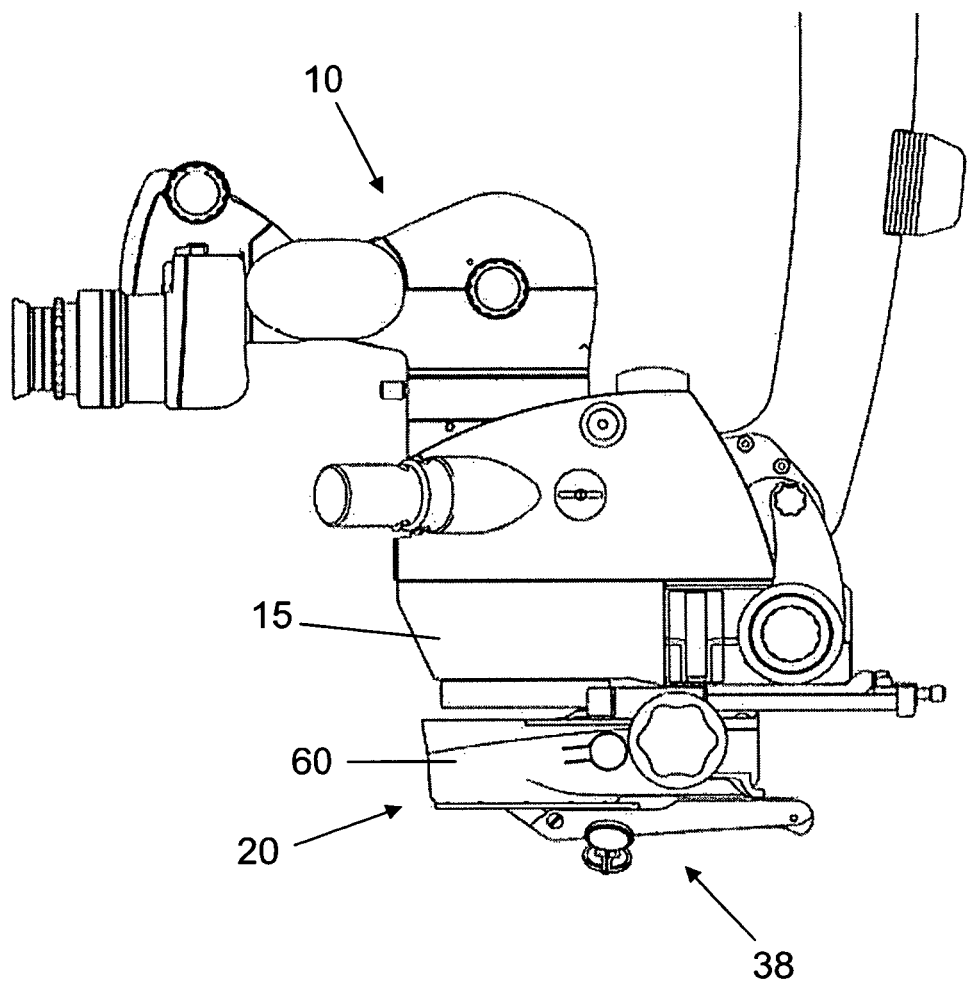
Figure 24:
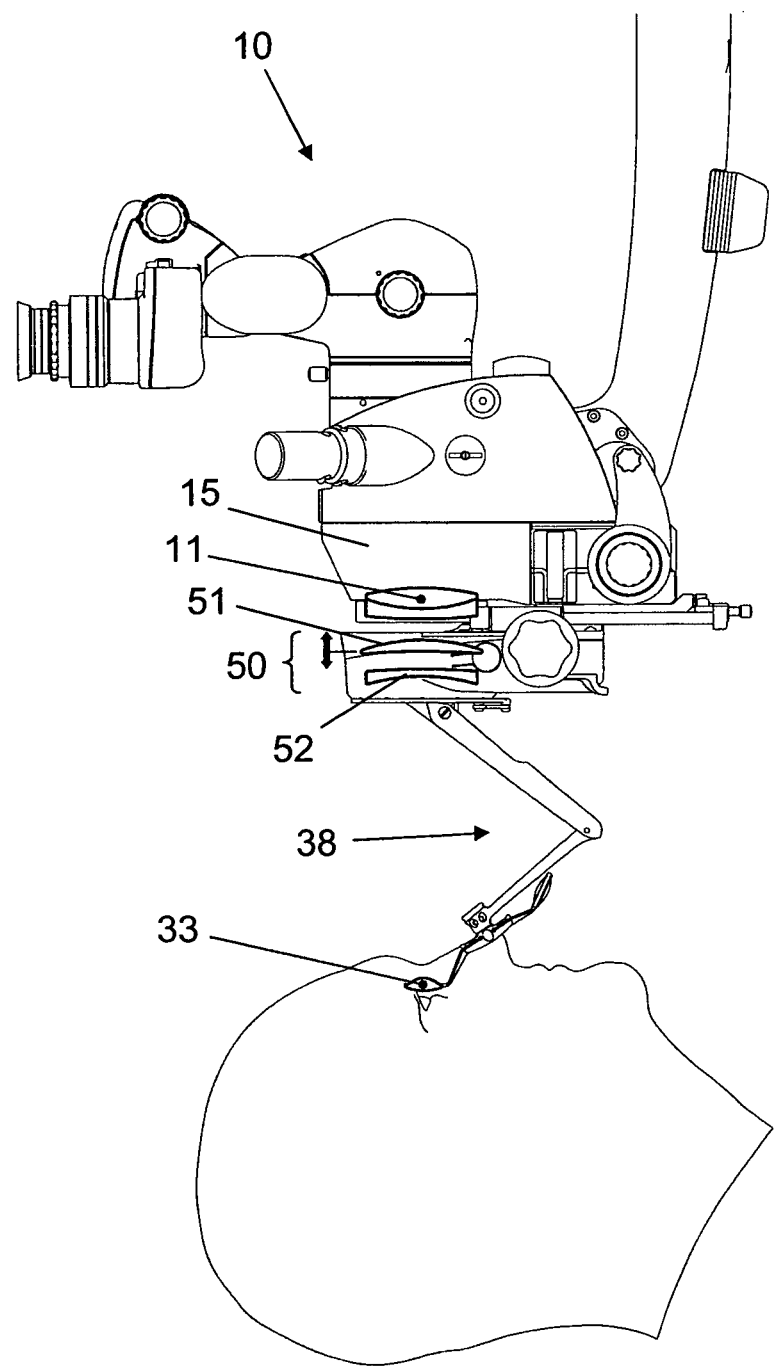
Figure 25:
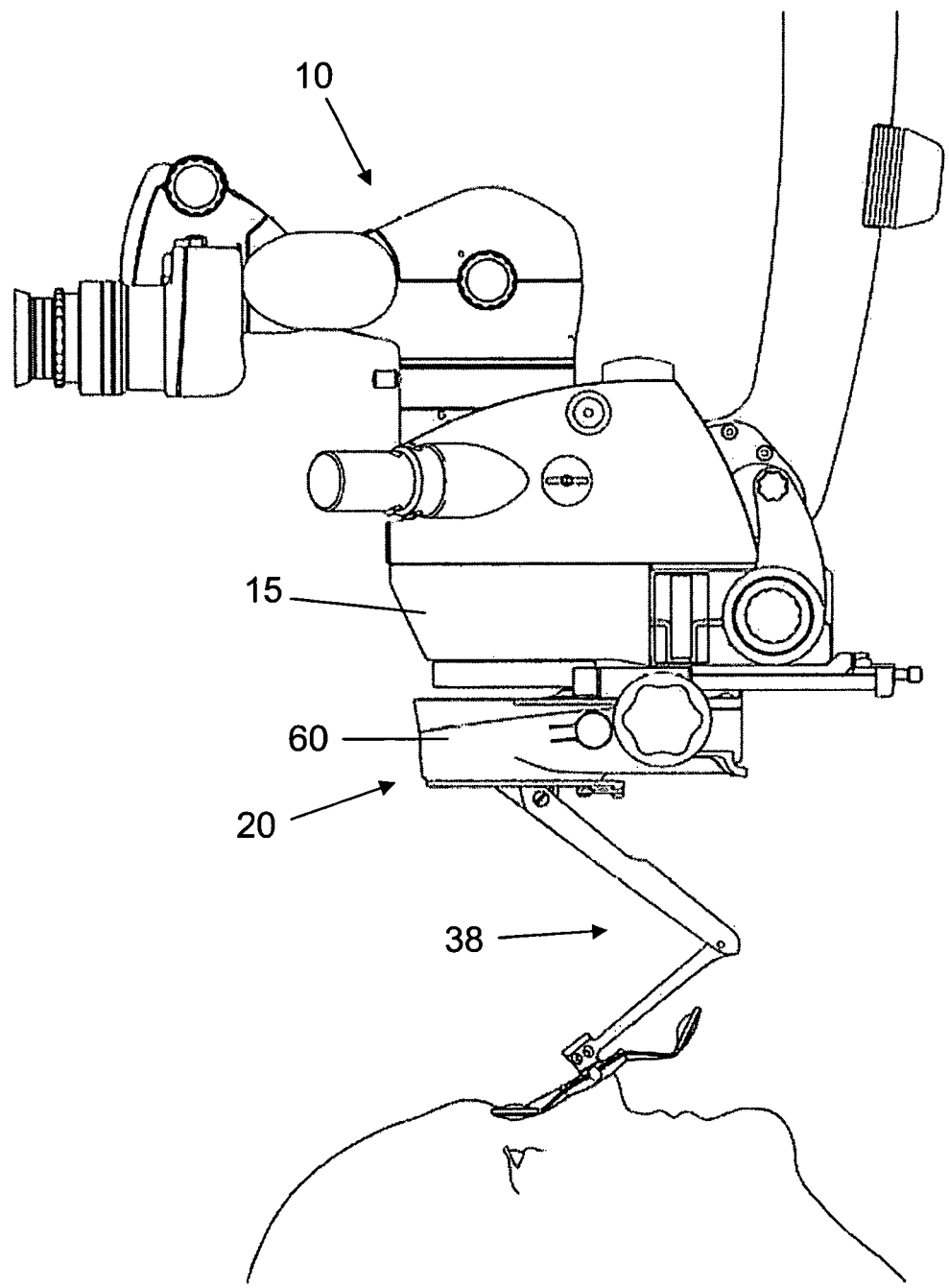

FIG. 22 shows a situation, which is suitable for working on the front segment of the eye. The operating microscope is focussed onto the plane of the iris of the patient's eye when the front-lens attachment is swung out and the focussing optics are moved out from the beam path. FIG. 23 shows the situation for working with indirect contact lenses, whereby a contact lens, of course, is not shown explicitly. The focussing device is swung in and the lens changer is found in a park position. FIG. 24 shows the arrangement in principle of the optical components of the front-lens attachment in the case of indirect contact-free ophthalmoscopy with an operating microscope. The ophthalmoscopic magnifying lens has been swung in, in fact coaxial to the optical axis and at a fixed, defined distance to the microscope and thus also to the patient's eye, this distance being dependent on the refractive power of the ophthalmoscopic magnifying lens. The distance to the patient's eye is selected so that an optimal, i.e., a frame-filling imaging is achieved without vignetting. Usually, a sharp image does not exist at this time point. When needed, the retaining element can be employed, in particular, it can be turned or rotated, in order to change the lens. This is shown in connection with FIG. 25. There, one or the other ophthalmoscopic magnifying lens, as desired, has been changed/swung in, in fact coaxial to the optical axis and at a fixed, defined distance to the microscope and thus also to the patient's eye, this distance being dependent on the refractive power of the ophthalmoscopic magnifying lens. The distance to the patient's eye is selected so that an optimal, i.e., a frame-filling imaging is achieved without vignetting. Usually, a sharp image does not exist at this time point.

Subsequently, the focussing optics are adjusted in order to sharpen the system to an intermediate image of the fundus of the eye or the region of the vitreous body (x mm over the retina), this image being generated by the ophthalmoscopic magnifying lens.

The position of the intermediate image plane is thus dependent on the type or the refractive power of the ophthalmoscopic magnifying lens, on the refractive error of the eye being observed, on the region/segment of the eye being observed, on anomalies of the eye, or on the distance between the ophthalmoscopic magnifying lens and the eye.

Thus, with an appropriate positioning of the ophthalmoscopic magnifying lens or a contact lens, it is possible to observe the fundus of the eye under the most varied conditions and for different ophthalmoscopic magnifying lenses or contact lenses without positional changes of the observation device, and the distance between the patient's eye and the microscope remains unchanged. A rapid and uncomplicated change between observing the front of the eye and the fundus results from this. In addition, such a system can be aligned and manipulated in a simple manner. The position of the pupil is focussed and manipulated by means of two movements that are decoupled.

The construction of the front-lens attachment shown in the figures can be produced in a simple way, and likewise it can be attached to and detached from the operating microscope in a simple manner. Because the positioning components can pivot around the joint, the front-lens attachment can be completely folded up, so that it can be held in a very space-saving manner on the operating microscope, particularly when it is not needed. Since the first positioning component is also disposed on the operating microscope via the fastening means so that it can pivot, the retaining device with the lens elements can be swung in a simple way into a region where these elements do not interfere with the work. In addition, the necessary structural space can be reduced. The front-lens attachment can be operated in a simple way and can move into the different positions without the need for special drives for this purpose.

LIST OF REFERENCE NUMBERS

10 Optical observation device (operating microscope)
11 Objective
12 Fastening region
13 Fastening leg
14 Fastening leg
15 Microscope body
20 Front-lens attachment
21 Positioning device
22 Positioning component (first positioning component)
23 Leg
24 Leg
25 Uptake space
26 End of the (first) positioning component
27 End of the (first) positioning component
28 Positioning component (second positioning component)
29 End of the (second) positioning component
30 End of the (second) positioning component
31 Joint (rotating joint)
32 Retaining element (retaining arm)
33 First lens element (ophthalmoscopic magnifying lens)
34 Second lens element (ophthalmoscopic magnifying lens)
35 Fastening means
36 First pivoting direction
37 Second pivoting direction
38 Retaining device
39 Direction of rotation
40 Direction of folding or aperture angle
41 Direction of rotation
42 Lens uptake
43 Lens holder (first lens element)
44 Lens holder (second lens element)
45 Direction of insertion
46 Direction of insertion
47 Lens mount
48 Turret attachment
49 Axis of rotation of the turret attachment
50 Focussing device
51 Optical component (positive component)
52 Optical component (negative component)
53 Direction of plugging on
54 Direction of displacement
60 Covering cap
61 Direction of plugging on
62 Fixing device
63 Unlocking button
64 Direction of unlocking
A Excerpt from the optical observation device according to FIG. 6

The invention claimed is:
1. A front-lens attachment for an optical observation device, in particular for a microscope, with a focussing device and with a retaining device, having a retaining element, on which at least one lens element is disposed, as well as further having a positioning device for positioning the retaining element and the at least one lens element disposed thereon relative to an optical observation device and/or focussing device, wherein retaining element is disposed on positioning device, is hereby characterized in that at least one covering cap is provided for focussing device to which retaining device is fastened and that the at least one covering cap is joined with focussing device.

2. The front-lens attachment according to claim 1, further characterized in that the covering cap is joined with focussing device in a detachable manner.

3. The front-lens attachment according to claim 1, further characterized in that focussing device has at least one optical component for focussing an observation device onto the intermediate image of the at least one lens element.

4. The front-lens attachment according to claim 1, further characterized in that retaining device is disposed in a detachable manner on covering cap.

5. The front-lens attachment according to claim 1, further characterized in that retaining device is disposed on covering cap in a rotatable and/or pivotable and/or linearly movable manner.

6. The front-lens attachment according to claim 1, further characterized in that positioning device has at least two positioning components, which are joined together via a joint.

7. The front-lens attachment according to claim 1, further characterized in that two or more lens elements are disposed on retaining element.

8. The front-lens attachment according to claim 1, further characterized in that at least one lens element is designed as an ophthalmoscopic magnifying lens.

9. The front-lens attachment according to claim 1, further characterized in that retaining element is designed as a retaining arm.

10. The front-lens attachment according to claim 1, further characterized in that retaining element is disposed on positioning device in a rotatable manner.

11. Use of a front-lens attachment according to claim 1 for indirect contact-free ophthalmology or indirect ophthalmology with contact.

12. An optical observation device, in particular a microscope, is hereby characterized in that it has at least a front-lens attachment according to claim 1.

13. The optical observation device according to claim 12, further characterized in that it has an objective and that the front-lens attachment is disposed in region surrounding objective on optical observation device.

14. The optical observation device according to claim 12, further characterized in that front-lens attachment is disposed in a pivotable and/or rotatable and/or linearly movable manner on optical observation device.

15. The optical observation device according to claim 12, further characterized in that focussing device is disposed in a detachable manner on optical observation device.

16. The optical observation device according to claim 12, further characterized in that it is designed as an operating microscope, in particular, as an operating microscope for ophthalmology.

17. A turret attachment for the rotatable arrangement of at least two lens elements on a front-lens attachment for an optical observation device, in particular, by a rotatable arrangement on a front-lens attachment according to claim 1, is hereby characterized in that turret attachment has a single retaining element that can rotate around an axis of rotation, on which the at least two lens elements are disposed.

18. The turret attachment according to claim 17, further characterized in that retaining element is designed as a lens uptake, that the at least two lens elements are each disposed on a lens holder and are disposed on lens uptake via the holders, particularly in a detachable manner.

19. The turret attachment according to claim 18, further characterized in that at least one of the lens holders has a curve-shaped course or an angular course, or a bent course, in at least one region.

20. The turret attachment according to claim 17, further characterized in that the axis of rotation of the turret attachment has an inclined course relative to an optical axis of the observation device.

21. An optical observation device, in particular a microscope, is hereby characterized in that it has at least a turret attachment according to claim 17.

22. Use of a turret attachment according to claim 17 for indirect contact-free ophthalmology or indirect ophthalmology with contact.

23. A front-lens attachment for an optical observation device, in particular for a microscope, with a retaining device, having a retaining element, on which at least one lens element is disposed, a positioning device for positioning the retaining element and the at least one lens element disposed thereon, relative to an optical observation device, wherein the retaining element is disposed on the positioning device, and with a fastening means for fastening the retaining device to the front-lens attachment, is hereby characterized in that the positioning device has at least two positioning components, which are joined together via a joint, in that the positioning device has a first positioning component, which has on one end thereof a joint element for articulated joining with a second positioning component, in that the fastening means is provided on the other end of the first positioning component, in that the second positioning component has on one end thereof a joint element for articulating joining with the first positioning component, and in that the retaining element is disposed on the other end of the second positioning component.

24. The front-lens attachment according to claim 23, further characterized in that retaining device is disposed in a detachable manner on front-lens attachment.

25. The front-lens attachment according to claim 23, further characterized in that retaining device is disposed on front-lens attachment in a rotatable and/or pivotable and/or linearly movable manner.

26. The front-lens attachment according to claim 23, further characterized in that positioning components are joined together via a rotating joint so that they can move in a pivoting manner.

27. The front-lens attachment according to claim 23, further characterized in that positioning components are joined together in an articulated manner in such way that they can be folded up or spread apart.

28. The front-lens attachment according to claim 23, further characterized in that positioning device has two positioning components, that a first positioning component has two legs distanced from one another, which bound an uptake space and that the other, second positioning component is joined with first positioning component via joint in such a way that it can be folded into the uptake space of the first positioning component.

29. An optical observation device, in particular a microscope, is hereby characterized in that it has at least a front-lens attachment according to claim 23, and that, in addition, a focussing device is provided, which is integrated into the optical observation device.

30. An optical observation device, in particular a microscope, is hereby characterized in that it has at least a front-lens attachment according to claim 23.

31. Use of a front-lens attachment according to claim 23 for indirect contact-free ophthalmology or indirect ophthalmology with contact.

* * * * *